(12) United States Patent
Allbritton et al.

(10) Patent No.: US 9,765,291 B2
(45) Date of Patent: Sep. 19, 2017

(54) ARRAY OF MICROMOLDED STRUCTURES FOR SORTING ADHERENT CELLS

(71) Applicant: The University of North Carolina at Chapel Hill, Chapel Hill, NC (US)

(72) Inventors: Nancy Allbritton, Chapel Hill, NC (US); Christopher Sims, Chapel Hill, NC (US); Yuli Wang, Cary, NC (US); Pavak Kirit Shah, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/714,620

(22) Filed: May 18, 2015

(65) Prior Publication Data
US 2015/0251151 A1 Sep. 10, 2015

Related U.S. Application Data

(60) Division of application No. 13/513,310, filed on Jun. 1, 2012, now Pat. No. 9,068,155, which is a
(Continued)

(51) Int. Cl.
*B01L 3/00* (2006.01)
*C12M 1/32* (2006.01)
(Continued)

(52) U.S. Cl.
CPC .......... *C12M 23/12* (2013.01); *B01J 19/0046* (2013.01); *C12M 23/20* (2013.01);
(Continued)

(58) Field of Classification Search
CPC ...... C12M 23/12; C12M 23/20; C12M 23/22; C12M 25/16; B01J 19/0046
(Continued)

(56) References Cited

U.S. PATENT DOCUMENTS 4,883,642 A 11/1989 Bisconte
5,858,770 A 1/1999 Perlman
(Continued)

FOREIGN PATENT DOCUMENTS

WO 2007127990 A2 11/2007
WO 2009018167 A1 2/2009
(Continued)

OTHER PUBLICATIONS

Wang Y et al. Collection and expansion of single cells and colonies released from a micropallet array. Analytical Chemistry, Mar. 15, 2007; 79(6): 2359-2366.
(Continued)

*Primary Examiner* — Jill Warden
*Assistant Examiner* — Brittany Fisher
(74) *Attorney, Agent, or Firm* — Michael G. Johnston; Moore & Van Allen PLLC

(57) ABSTRACT

An apparatus for collecting or culturing cells or cell colonies includes: a common substrate formed from a flexible resilient polymeric material and having a plurality of wells formed therein; and a plurality of rigid cell carriers releasably connected to said common substrate, with said carriers arranged in the form of an array, and with each of the carriers resiliently received in one of the wells. A method of collecting or culturing cells or cell colonies with such an apparatus is carried out by depositing a liquid media carrying cells on the apparatus so that said cells settle on or adhere to said the carriers; and then (c) releasing at least one selected carrier having said cells thereon by gradual application of release energy to each carrier from the cavity in which it is received (e.g., by pushing with a probe).

10 Claims, 14 Drawing Sheets

Related U.S. Application Data continuation-in-part of application No. PCT/US2011/025018, filed on Feb. 16, 2011.

(60) Provisional application No. 61/305,067, filed on Feb. 16, 2010, provisional application No. 61/375,596, filed on Aug. 20, 2010.

(51) Int. Cl.
*C12M 1/12* (2006.01)
*B01J 19/00* (2006.01)
*C12M 1/00* (2006.01)

(52) U.S. Cl.
CPC ............ *C12M 23/22* (2013.01); *C12M 25/04* (2013.01); *C12M 25/16* (2013.01); *C12M 47/02* (2013.01); *C12M 47/04* (2013.01); *B01J 2219/00452* (2013.01); *B01J 2219/00743* (2013.01)

(58) Field of Classification Search
USPC ........................................................ 422/500
See application file for complete search history.

(56) References Cited

U.S. PATENT DOCUMENTS

| | | | |
|---|---|---|---|
| 6,455,310 B1 * | 9/2002 | Barbera-Guillem ... | C12M 23/10 435/288.3 |
| 6,585,939 B1 | 7/2003 | Dapprich | |
| 7,070,740 B1 | 7/2006 | Matson et al. | |
| 9,068,155 B2 | 6/2015 | Allbritton et al. | |
| 2002/0173033 A1 | 11/2002 | Hammerick et al. | |
| 2006/0010510 A1 * | 1/2006 | Christmann ....... | A01K 67/0275 800/19 |
| 2006/0154233 A1 * | 7/2006 | Deutsch ............ | B01L 3/502761 435/4 |
| 2007/0238122 A1 * | 10/2007 | Allbritton ............ | B01L 3/5085 435/6.11 |
| 2007/0269850 A1 | 11/2007 | Crespi et al. | |
| 2008/0108123 A1 | 5/2008 | Imamura et al. | |
| 2008/0193536 A1 | 8/2008 | Khademhosseini et al. | |

FOREIGN PATENT DOCUMENTS

| | | |
|---|---|---|
| WO | 2010068743 A1 | 6/2010 |
| WO | 2010085751 A2 | 7/2010 |
| WO | PCT/US2011/025018 | 2/2011 |

OTHER PUBLICATIONS

Charnley M. et al. Integration column: microwell arrays for mammalian cell culture. Integrative Biology. 2009; 1: 625-634.

Kovac JR et al. Image-Based Cell Sorting Using Optofluidicc Cell Sorting. Analytical Chemistry. 2007, 79, 9321-9330.

Love JC et al. A microengraving method for rapid selection of single cells producing antigen-specific antibodies. Nature Biotechnology 2006, 24, 703-707.

Luo C et al. The combination of optical tweezers and microwell array for cells physical manipulation and localization in microfluidic device. Biomedical Microdevices 2007, 9(4), 573-578.

Moeller H-C et al. A microwell array system for stem cell culture. Biomaterials 2008, 29(6), 752-763.

Mohr JC et al. 3-D microwell culture of human embryonic stem cells. Biomaterials 2006, 27(36), 6032-6042.

Pai J-H et al. Photoresist with low fluorescence for bioanalytical applications. Analytical Chemistry 2007, 79, 8774-8780.

Rettig JR et al. Large-scale single-cell trapping and imaging using microwell arrays. Analytical Chemistry 2005, 77(17), 5628-5634.

Salazar GT et al. Micropallet arrays for the separation of single, adherent cells. Analytical Chemistry 2007, 79, 682-687.

Salazar GT et al. Characterization of the laser-based release of micropallets from arrays. Journal of Biomedical Optics 2008, 13(3), 034007-1-034007-9.

Shadpour H. et al. Sorting and Expansion of Murine Embryonic Stem Cell Colonies Using Micropallet Arrays. Cytometry Part A 2009, 75A(2), 121-129.

Shadpour H. et al. Enrichment and Expansion of Cells Using Antibody Coated Micropallet Arrays. Cytometry Part A 2009, 75A(7), 609-618.

Wang Y. et al. Broadening cell selection criteria with micropallet arrays of adherent cells, Cytometry Part A 2007, 71A(10), 866-874.

Wang Y. et al. Micropallet arrays with poly(ethylene glycol) walls. Lab on a Chip 2008(8), 734-740.

Wang Y. et al. Simple photografting method to chemically modify and micropattern the surface of SU-8 photoresist. Langmuir 2006, 22(6), 2719-2725.

Wang Y et al. Micropatterning of living cells on a heterogeneously wetted surface. Langmuir 2006, 22(19), 8257-8262.

Wang Y et al. Surface graft polymerization of SU-8 for bio-MEMS applications. Journal of Micromechanics and Microengineering 2007, 17, 1371-1380.

Gach PC et al. Isolation and manipulation of living adherent cells by micromolded magnetic rafts. Biomicrofluidics 2011. 5: 032002-1-032002-11.

Gunn NM et al. Ferromagnetic micropallets for magnetic capture of single adherent cells. Langmuir 2010, 26(22), 17703-17711.

Love et al. A microengraving method for rapid selection of single cells producing antigen-specific antibodies, Nature Biotechnology 24(6): 703-707, 2006.

International Search Report and Written Opinion, PCT/US2011/025018, mailed May 12, 2011.

U.S. Appl. No. 14/714,597, Office Action, Sep. 6, 2016.

Nam, Hye Jin, et al., Gold nanostructures on chemically reinforced PDMS microwell arrays, 2010, Applied Surface Science, pp. 2066-2072, vol. 256.

Wang, Y., et al., Micromolded arrays for separation of adherent cells, 2010, Lab on a Chip, pp. 2917-2924, vol. 10.

Gach, Philip C., Transparent magnetic photoresists for bioanalytical applications, Biomaterials, 2010, pp. 8810-8817, vol. 31.

Pai, Jeng-Hao, et al., Microtable arrays for culture and isolation of cell colonies, Anal Bioanal Chem, 2010, pp. 2595-2604, vol. 398.

The University of North Carolina at Chapel Hill, European Patent Application No. 11745150.0, Extended European Search Report, Dec. 23, 2016.

The University of North Carolina at Chapel Hill, Canadian Patent Application No. 2,789,761, Office Action, Feb. 24, 2017.

U.S. Appl. No. 61/375,596, filed Aug. 20, 2010.

U.S. Appl. No. 61/305,067, filed Feb. 16, 2010.

\* cited by examiner

Figure 14. Scheme for the magnetic collection of microrafts.

ARRAY OF MICROMOLDED STRUCTURES FOR SORTING ADHERENT CELLS

RELATED APPLICATIONS

This application is a divisional application of U.S. application Ser. No. 13/513,310 filed Jun. 1, 2012, which is a continuation-in-part application of PCT Application No. PCT/US2011/025018, filed Feb. 16, 2011, which in turn claims the benefit of US Provisional Applications No. 61/375,596, filed Aug. 20, 2010, and 61/305,067, filed Feb. 16, 2010, the disclosures of all of which are incorporated by reference herein in their entirety.

STATEMENT OF FEDERAL SUPPORT

This invention was made with Government support under grant numbers EB007612, HG004843, and EB012549 from the National Institutes of Health. The US Government has certain rights to this invention.

BACKGROUND OF THE INVENTION

The selection and isolation of single cells from a mixed population is a common procedure performed throughout biomedical research. For example, during the development of cell lines that are genetically engineered, derived from stem cells, or grown from patient cell lines, single cells must be isolated and then cloned to form a homogeneous population. A variety of strategies exist to selectively identify and collect nonadherent cells from a mixed population, including fluorescence activated cell sorting (FACS), limiting dilution, panning, column chromatography and magnetic sorting; furthermore, new techniques based on microfluidics and dielectrophoresis show promise in this area.[1-6] To address the need to collect pure or enriched populations of adherent cells, investigators use these procedures by disaggregating or stripping the cells from their growth surface to create cell suspensions. Unfortunately, enzymatic or mechanical release imposes significant drawbacks including loss of cell morphology, removal of cell surface markers, damage to cell membranes, alterations in cellular physiology and loss of viability.[7-14]

New techniques for adherent, mammalian cell selection address some of the challenges but remain limited for living cells. Laser capture microdissection (LCM) (Arcturus; Mountain View, Calif.) has enabled single cells or small groups of selected cells to the obtained from tissue sections for genetic and proteomic studies, although most applications utilize fixed or frozen specimens.[15] Protocols for use with live cells have been published, but are very low throughput and not suitable for isolating large numbers of single, living cells.[16] Most applications of LCM utilize fixed or frozen specimens.[15-18] Thus, these techniques have only partially met the needs of investigators for the positive selection of adherent, mammalian cells. P.A.L.M. Microlaser Technologies (Bernried, Germany) markets an instrument that uses a laser to cut out a region of interest from a tissue section and then generate a shock wave that "catapults" the cells into an overlying collection device.[17] Again most of the work with this technique has utilized fixed specimens, but collection of living cells has been demonstrated.[18] Cells are subjected to stress due to the direct effects of the shock wave and desiccation from removal of fluid overlying the sample during collection. ClonePix (Genetix, Hampshire, UK) is an automated system that uses image recognition to guide a suction pipette that aspirates colonies of loosely adherent cells from plates. The system requires cells that grow in loosely adherent clusters or suspension-adapted versions of adherent cells growing in a semi-solid methylcellulose media, thus it is not applicable to the vast majority of mammalian cells.

Recently, the Allbritton group developed an array technology for sorting adherent cells.[19-23] This cell sorting strategy uses arrays of releasable, microfabricated elements, termed pallets, formed from the biocompatible epoxy photoresist, either formulated from EPON SU-8 or 1002F epoxy resins.[19, 24] The epoxy is photolithographically defined on a standard microscope slide to create the pallet array. The pallets can be varied in size from tens to hundreds of microns to provide an adequate growth area for single cells or large colonies. In addition, the pallet surfaces can be modified with proteins or gels to enhance cell attachment and growth.[19, 25, 26] To culture cells on these arrays, cells are initially placed in suspension, but are allowed to settle and grow on individual pallets prior to analysis. When cells are plated on the array, the virtual air wall or polyethylene glycol hydrogel wall limit the location for cell attachment to the upper pallet surface.[19, 23] Since the array is transparent, cells can be analyzed by standard microscopy techniques during culture. Subsequent to analysis, individual pallets containing the desired cells are released from the array using a pulsed laser and are then collected.[20, 22] Recent studies of the selection and expansion of single cells have demonstrated a high rate of viability after laser-based release and exceptional success in clonal expansion of individual, sorted cells.[21, 22] The approach makes possible a range of cell selection criteria for determining cells of interest (e.g. phenotrypic and temporal criteria and other characteristics) not accessible by alternative methods.[22] The pallet array has recently been used as a platform for culturing and sorting stem cell, and sorting cells based on antibody affinity.[27, 28]

Although some unique advantages have been demonstrated for the pallet array over other cell sorting technologies, several limitations need to be overcome before it can be widely accepted by the biology research community. The most serious limitation is that an expensive optical system is required to release a target pallet from the array. The optical system (including pulsed laser, beam splitter, mirror and lens) must be precisely aligned and maintained. To effectively release a pallet from the glass surface on which it is formed, the beam of the laser must be focused precisely at the interface between pallet and glass within a distance of a few micrometers.[29] To assist the user to find the right laser focal plane, indicators need to be built on the pallet array which adds complexity to fabrication. The shock wave generated by the laser is detrimental to the viability of cells, and as a result the energy of each laser pulse must be restricted to be less than 5 µJ in order to maintain high post-sort cell viability. However, a very low energy of release requires precise control of the adhesion force between the pallet and glass to keep pallets attached to the array until released is desired. In addition to the limitations required for laser-based release, the pallet array itself has drawbacks. First, the pallet array is made from photoresist having autofluorescence in the range of 480-520 nm, which coincides with the range of wavelengths of the most frequently used dyes (e.g. FITC, Oregon green, Alexa Fluor 488, etc) for fluorescence imaging.[22, 24] Second, the fabrication of the pallet array is expensive and complicated, since the whole fabrication process needs a clean environment and expensive microfabrication tools including mask aligner, photoresist spin coater, metal evaporator, and plasma cleaner.[19]

Accordingly, there is a need for new ways to construct microcarriers useful for cell sorting.

SUMMARY OF THE INVENTION

A first aspect of the invention is an apparatus for collecting or culturing cells or cell colonies. The apparatus comprises a common substrate formed from a flexible resilient polymeric material and having a plurality of wells formed therein; and a plurality of rigid cell carriers releasably connected to said common substrate, with said carriers arranged in the form of an array, and with each of said carriers resiliently received in one of said wells.

A further aspect of the invention is a method of collecting or culturing cells or cell colonies, comprising: (a) providing an apparatus comprising a common substrate, said substrate formed from an elastomer and having a plurality of cavities formed therein in the form of an array, and a plurality of cell carriers releasably received in said carriers, (b) depositing a liquid media carrying said cells on said apparatus so that said cells settle on or adhere to said cell carriers; and then (c) releasing at least one selected carrier having said cells thereon by gradual application of release energy to each of said at least one carrier from the cavity in which it is received.

In some embodiments, the carriers are coated with a biologically active molecule (that is, one or more) on at least the top surface thereof (e.g., all of the top surface, a major or minor portion of the top surface, etc.)

The present invention is explained in greater detail in the drawings herein and the specification set forth below. The disclosures of all United States patent references cited herein are to be incorporated by reference herein in their entirety.

DETAILED DESCRIPTION OF THE INVENTION

Figure 1:
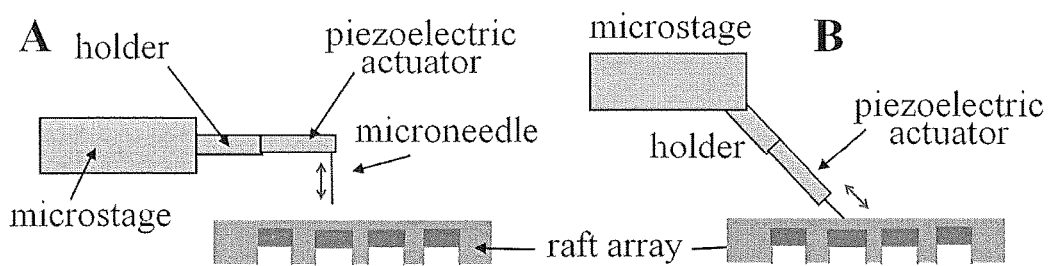
FIG. 1. Shown are schematics (A,B) of raft release hardware and geometry.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

"Interdigitated" as used herein with respect to carriers or microcups in an array means that the pattern of the array is staggered or off-set (typically in a uniform or repeating pattern) so that gap intersections are reduced in size and the opportunity for cells to settle at such intersections is reduced. Interdigitation can be achieved by one or more of a variety of means. The microcups can be hexagonal or triangular in cross-section; the microcups, when square or rectangular, can be offset from one another in adjacent row. The microcups can be provided with one or more vertical ridges that, when arranged in an array, interdigitates with gaps between microcups in adjacent rows. Numerous variations on the foregoing will be apparent to those skilled in the art.

"Cells" for carrying out the present invention are, in general, live cells, and can be any type of cell, including animal (e.g., mammal, bird, reptile, amphibian), plant, or other microbial cell (e.g., yeast, gram negative bacteria, gram positive bacteria, fungi, mold, algae, etc.).

"Liquid media" for carrying out the present invention, in which cells are carried for depositing on an array as described herein (and specifically within the cavities of the microcups) may be any suitable, typically aqueous, liquid, including saline solution, buffer solutions, Ringer's solution, growth media, and biological samples such as blood, urine, saliva, etc. (which biological samples may optionally be partially purified, and/or have other diluents, media or reagents added thereto).

"Substrate" as used herein is, in general, a flexible or elastomeric substrate, and may be conveniently formed from a material in which cavities may be produced and the carrier molded directly therein. Examples include, but are not limited to, silicones (e.g., polydimethylsiloxane (or "PDMS"), Silastic, Texin and ChronoFlex silicone materials), polyurethane substrates, styrene-butadiene copolymer, polyolefin and polydiene elastomers, thermoplastic elastomers, other biomedical grade elastomers, etc.

"Biodegradable polymer" as used herein includes biodegradable polyesters and biodegradable aliphatic polymers. Numerous examples are known, including but not limited to those described in U.S. Pat. Nos. 7,879,356; 7,862,585; 7,846,987; 7,842,737; and 7,767,221. Particular examples include, but are not limited to, polymers that includes poly(lactic acid) (including poly(L-lactide) and poly(DL-lactide)), polyglycolide, poly(lactide-co-glycolide) (PLGA) (including poly(DL-lactide-co-glycolide)), poly(caprolactone) (PCL), poly[(R)-3-hydroxybutyric acid (PLA), poly (glycolic acid) (PGA), poly(ethylene glycol) (PEG), poly (hydroxy alkanoates) (PHA), dendritic polymers with acidic, hydroxyl and ester functional groups, modified polyesters, acetylated cellulose, starch, a starch derivative, a co-polymer of PLA and a modified polyester, or a combination thereof.

"Hydrogel" as used herein refers to a composition comprising a network of natural or synthetic polymer chains that are hydrophilic, and in which a significant amount of water is absorbed. Numerous examples are known, including but not limited to those described in U.S. Pat. Nos. 7,883,648; 7,858,375; 7,858,000; 7,842,498; 7,838,699; 7,780,897; and 7,776,240.

Arrays.

As noted above, the present invention is generally comprised of a common substrate formed from a flexible resilient polymeric material and having a plurality of wells formed therein; and a plurality of rigid cell carriers releasably connected to the common substrate, with said carriers arranged in the form of an array, and with each of the carriers resiliently received in one of said wells.

The cavities in said substrate can be separated by walls. The walls may be uniform or non-uniform and of any suitable dimension. In some embodiments, the walls have an average width of at least 2 micrometers, up to 5, 10, 100, 200, 500, or 1000 micrometers. In general, the walls have an average height of at least 2 or 5 micrometers, up to 200, 500, or 1000 micrometers.

The cavities in the substrate in some embodiments have floors. The floors can be uniform or non-uniform and of any suitable thickness. In some embodiments, the floors have an average thickness of from 2 or 5 to 200 or 500 micrometers.

In other embodiments, the floor is eliminated and the cavity is a continuous opening from the top surface of the substrate to the bottom surface of the substrate. Such arrays can be made in accordance with known techniques by, for example, from the substrate with such continuous cavities on top of a release layer.

The array may be in any suitable uniform or non-uniform arrangement, including but not limited to interdigitated arrays and/or tilings.

The substrate has a top surface, and the carriers are preferably positioned either below the top surface, or up at (that is, even with, or flush with) the top surface). Preferably the carriers do not protrude above the top surface of the substrate. This configuration can follow from one preferred way of making the array, by forming the substrate with the cavities and then casting the carriers in the cavities, as discussed further below.

The carriers are configured to release from said substrate upon mechanical distortion of said substrate: that is, the application of a gradual energy such as mechanical pushing or continuous vibration, in contrast to a "burst" of energy, as discussed further below. The carriers or rafts may be in any suitable geometry, including cylindrical, elliptical, triangular, rectangular, square, hexagonal, pentagonal, octagonal, etc., including combinations thereof. In some embodiments, the carriers have heights of at least 2 micrometers, up to 400 or 500 micrometers. In some embodiments, the carriers have maximum widths of at least 5 or 10 micrometers, up to 1000 micrometers.

The substrate can be produced by any suitable technique, such as printing or microprinting. The carriers can likewise be produced by any suitable technique, such as by casting the carriers in the cavities or wells formed during printing of the substrate. In some embodiments, the carriers have a concave top surface portion. While any desired physical or structural feature can be incorporated into the carrier top portion, alone or in combination, a concave top surface portion is conveniently formed by meniscus coating of the side walls of said wells or cavities in the substrate during the process of casting said carriers in those cavities or wells.

The carriers (also referred to as "rafts" herein) can be formed of any suitable material. The rafts are, in some embodiments, preferably transparent or semitransparent (e.g., visually transparent, optically transparent, optically transparent at certain wavelengths, and/or optionally containing elements or features that magnifies, reflects, refracts, absorbs or otherwise distorts light or certain wavelengths of light as light passes therethrough, etc.) A variety of polymers and other materials can generally satisfy the requirements for the microcarriers or rafts. Currently polystyrene (including copolymers thereof) and epoxy are preferred. A wide range of epoxies can be used including the epoxy novolac resins such as EPON 1001F, 1009F, and 1007F. These resins can be used alone or with crosslinkers. Preformulated epoxies, such as Loctite Hysol and other medical device epoxies can also be used. Medical device polymers such as polystyrene (including copolymers thereof, such as poly(styrene-co-acrylic acid) (PS-AA)), poly(methyl methacrylate), polycarbonate, and cyclic olefin copolymer can also be used as raft materials. Sol-gel materials, ceramics, and glasses (e.g., sodium silicate) can also be used as raft materials. Biodegradable polymers and hydrogels can also be used as raft materials. The rafts may be formed of a single material, may be a composite of two or more layers of different materials, etc. The rafts may be "doped" with one or more additional agents, such as growth factors (e.g., as in matrigel), magnetic or ferromagnetic particles or nanoparticles, live feeder cells, etc.

Methods of Use.

Arrays of the present invention are, in some respects, used in like manner as previous arrays, subject to some of the modifications described further herein.

The present invention provides a method of collecting or culturing cells or cell colonies, generally involving the steps of: (a) providing an apparatus comprising a common substrate, the substrate formed from an elastomer and having a plurality of wells formed therein in the form of an array, and a plurality of cell carriers releasably received in those wells, as described above; (b) depositing a liquid media carrying the cells (including but not limited to non-adherent cells) on apparatus so that the cells settle on or adhere to the cell carriers; and then (c) releasing at least one selected carrier having the cells thereon by application of release energy to each of the at least one carrier from the well in which it is received.

Release energy may be applied as a burst of energy, or may be applied in a gradual maimer. In some embodiments of the present invention release energy is applied gradually, for example, by gradual mechanical pushing or vibrating. In general, any suitable device for applying a release energy gradually may be employed. In some embodiments, sudden "bursts" of energy are less preferred because the resilient engagement of the carrier in the generally elastic substrate tends to serve as a "shock absorber" that resist release of the carrier by application of all but very large energy bursts (which then tend to release, for some (but not all) embodiments, undesirably large numbers of carriers). Hence, in some embodiments, release energy is typically applied over a duration of at least 1 millisecond (ms), at least 10 ms, at least 100 ms, and at least 1 second to achieve carrier or raft release.

In some embodiments, mechanical pushing is carried out by positioning a probe (e.g., a blunt probe, a needle, micropipette tip, etc), adjacent (e.g. above, below) beneath the common substrate and oriented towards the at least one selected carrier, and then progressively contacting the probe to the substrate. Progressively contacting may be carried out at any suitable rate of speed (as a non-limiting example, at a rate of 0.01 or 1 to 500 or 1000 m/s) until the at least one carrier is released therefrom. In some embodiments the probe does not pierce the substrate; in other embodiments the probe pierces the substrate and contacts and dislodges the at least one carrier.

As discussed further below, in some embodiments the pushing is aided by or guided by a microscope (e.g., an optical microscope, a fluorescent microscope). In such embodiments, the probe may be connected to or mounted on the microscope objective in a configuration that permits visualization of the selected carrier to be dislodged by the probe through the microscope objective as an aid or guide to carrying out the pushing or dislodgement of the selected carrier. The microscope may be a simple manual optical microscope, with pushing carried out manually, or a partially or fully automated microscope with pushing or dislodgement of the carrier achieved or carried out in an automated manner by movement of the objective (e.g., with a manual or automated XYZ drive stage, and/or with a drive or drive assembly included in the microscope objective assembly).

In some embodiments, the invention is configured and carried out so that cells are deposited on the apparatus at an efficiency of capture (that is, are received in carriers rather than on walls) of at least 40, 50, or 60 percent.

Control of Probe Movement.

Probe or microneedle movement can be provided by any suitable means, such as a miniaturized piezoelectric driver (Physique Instrumente GmbH, P-563) (FIG. 1) or similar piezoelectric device. Typically, these devices can travel up to 5 cm in the forward or reverse direction with velocities up to 200 m/s and step sizes as little as 5 um, while generating forces up to 0.2 N. The devices can be controlled by a 5V TTL signal. The microneedle is supported on the piezo-driven rod and an XYZ microstage by any suitable means, such as custom mounts or clamps. Movement of the microneedle is in some embodiments controlled using a standard digital board interfaced via Metamorph (Molecular Devices) or uManager (http://www.micro-manager.org/) software. If the piezomotor proves insufficient for a particular application, DC motor (for example, Pololu Robotics & Electronics, Las Vegas, Nev.) can be utilized using similar mounting and control software.

A third strategy is a commercially available microinjection system (Eppendorf) with the injection pipette replaced by the microneedle, since the required motions for the microneedle are similar to that of a microinjection pipette. Still other approaches for the application of release energy include an ultrasound transducer, which may be used to vibrate or gradually vibrate a carrier from its corresponding cavity.

Collection Plate and Scaffolding Support for the Microraft Array.

Since the substrate (which also serves as the mold for the microcarriers) is a flexible polymer, a scaffold may be used in some (but not all) embodiments to prevent sagging of the array during imaging and raft release. In addition, released rafts are generally collected for subsequent culture. A scaffold and collection plate are in some embodiments combined into a single unit. Support posts or walls are, for example, fabricated from 1002F photoresist or PDMS on a glass base using standard photolithography or soft lithography. If needed, high quality glass plates (Erie Scientific, Portsmouth, N.H.) that have a flatness with a variance of less than 1 micron over several centimeters of travel are utilized for the collection plate. Alternatively, a polycarbonate cassette is machined using a CNC tool to provide the scaffold as well as collection plate. A jig or clamp is provided to hold the raft array over the scaffolding during raft release. Special care can be paid to sterility of the array as necessary.

For the probe-based (e.g., needle-based) release, the amount of array sag can be large since needle movement in the z direction does not need to be precise; however, the constraints for imaging are much tighter even with low magnification objectives (0.63×, numerical aperture (NA) 0.15). The depth of field for this objective is 22 µm; therefore, the goal in some (but not all) embodiments is to limit the amount of sag in the array between support posts to ≤22 µm. PDMS is an example in the following discussions; however, similar strategies can be employed for other mold materials. Again, in other embodiments, some sag, or even considerable sag, is less problematic and no steps to avoid sag need be taken.

Three strategies can be utilized to reduce array sag. (1) Increase Young's modulus of the mold. A PDMS formulation with reduced elasticity or a Young's modulus of 10-15

Figure 2:
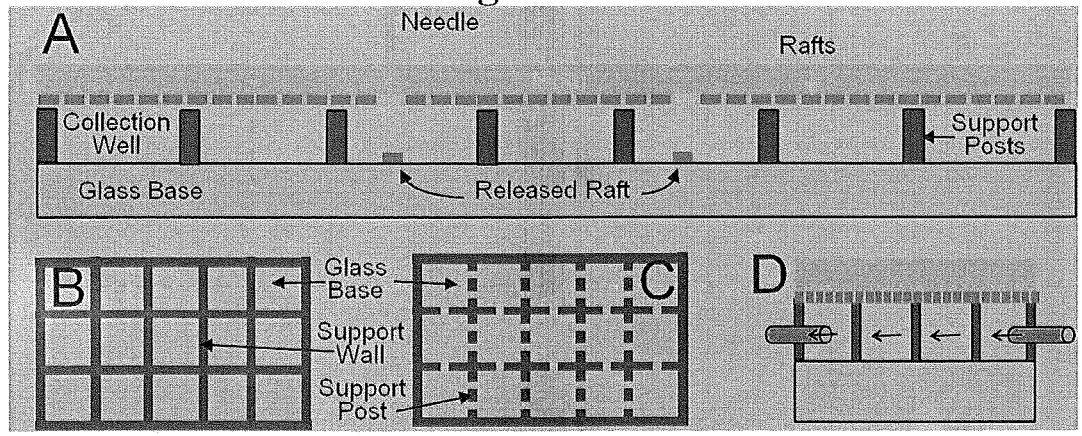
FIG. 2. Schematic of array scaffold and raft collection plate. A) Side view of the mold mated to the scaffold/collection plate. B & C) Top view of scaffold/collection plate only. Either support walls (B) or posts (C) are present. D) Side view of mated array and scaffold/collection plate with vias shown for array washing.

MPa (10-fold higher than that of Sylgard 184 PDMS) can be used. Simulations using Comsol suggest that array sag can be reduced to less than 10 um with support posts 15 mm apart. (2) In plane stretching of the PDMS mold. The substrate can be stretched along the axes parallel to the array surface to offset the out-of-plane sag (z-axis). If necessary, a film laminating instrument will be used to stretch the array uniformly before it is attached to a scaffold. (3) Decrease the scaffold spacing. The distance between the posts or walls for array support (FIG. 2) can be varied to increase or decrease the degree of array sag as necessary.

Rafts released into the collection wells can be cultured in the collection plate or retrieved for culture in standard multiwell plates. If cells floating in the medium (not attached to a surface) act as a source of contamination, the array can be washed extensively prior to release or vial can be inserted on either side of the collection plate for washing the array (FIG. 2D).

Coatings.

In some embodiments, one or more biologically active molecules is applied to or coated on the rafts (particularly, the top surface or layer of the raft). Different rafts in the same device may be coated with the same, or a different, molecule. Examples of such biomolecules include, but are not limited to, a peptide, a protein, a carbohydrate, a nucleic acid, a lipid, a polysaccharide, a hormone, an extracellular matrix molecule, a cell adhesion molecule, a natural polymer, an enzyme, an antibody, an antigen, a polynucleotide, a growth factor, a synthetic polymer, polylysine, a drug, etc., including combinations thereof. Coating may be carried out by any suitable technique, including but not limited to simple adsorption and covalent coupling. See, e.g., U.S. Pat. No. 7,579,179. More particular examples of biologically active molecules include, but are not limited to, fibronectin, laminin, thrombospondin, collagen including collagen IV, elastin, tenascin, vitronectin; carbohydrates, and lipids; fibrinogen, tenascin; bovine pituitary extract, epidermal growth factor, hepatocyte growth factor, keratinocyte growth factor, and hydrocortisone. (See, e.g., U.S. Pat. No. 7,455,816; see also U.S. Pat. No. 7,713,734); pharmaceutical preparations or compounds; substances which influence the properties of biological cells; messengers; growth factors (e.g., vascular endothelial growth factor, bone morphogenic factor beta, epidermal growth factor, endothelial growth factor, platelet-derived growth factor, neural growth factor, fibroblast growth factor, insulin growth factor, or transforming growth factor); differentiation factors (e.g., neurotrophin, colony stimulating factor, transforming growth factor); antigens; allergens; etc. (See, e.g., U.S. Pat. No. 7,455,816; see also U.S. Pat. No. 7,704,740).

Composite Carriers.

Carriers of the present invention. may be composites of two or more (e.g., 2, 3, 4, 5, 6) layers, with each layer formed of a different material, or having a different composition, than the immediately adjacent layer or layers. This feature can be used to incorporate a variety of advantageous structural and/or functional features into the carrier.

For example, in some embodiments, the carriers may be made magnetic or ferromagnetic by incorporating magnetic or ferromagnetic particles or nanoparticles into one or more layers of the carrier. If desired, a barrier layer can be provided between the layer(s) in which such particles or nanoparticles are incorporated, and the cell-supporting surface, to inhibit the transfer of particles or nanoparticles from the carriers to the cells.

In some embodiments, the carriers, or one or more layers of the carriers, comprise polystyrene (including copolymers thereof). In some embodiments, the carriers, or one or more layers of the carriers, comprise an anionic transparent magnetic polystyrene (e.g., a polystyrene copolymer incorporating an anionic comonomer such as acrylic acid, and containing magnetic or ferromagnetic particles or nanoparticles).

In some embodiments, the carriers comprise a rigid lower layer (sufficiently rigid to facilitate the mechanical displacement of the carrier from the elastomeric support; e.g., formed of a rigid polymer such as polystyrene, ceramic or glass, etc.); optionally, one or more intervening layers; and a cell-growth compatible upper layer on which cells can be grown such as a gel layer (e.g., matrigel or hydrogel, containing growth factors, antibodies, or the like). For example, the cell growth-compatible upper layer may comprise polystyrene such as an anionic polystyrene), a hydrogel (optionally containing live feeder cells to facilitate the growth of cells thereon, in any suitable amount, e.g., from 1, 5 or 10 to 100 or 1,000 cells per carrier, such as murine embryonic fibroblasts); a biodegradable polymer, a biologically active material or biomolecule as described above, etc.

The present invention is explained in greater detail in the following non-limiting Examples.

EXAMPLE 1

As one non-limiting example of the invention, we describe here an improved technology for creating an array of individually releasable elements which overcomes the above limitations. Instead of fabricating pallets on glass using photolithography and photoresist, we use an array of microwells made from PDMS as the template to micromold the rafts. The micromolded raft contains no photoinitiator and therefore has a low autofluorescence background. The micromolding process does not require any microfabrication tool, so the fabrication becomes extremely simple and inexpensive. Since the raft is located inside the microwell, cells can fall into the microwell and then attach, thus eliminating the necessity of using a virtual air wall or PEG hydrogel wall to localize cell attachment. The most important improvement is to replace the expensive optical system with a low-cost needle release system. A selected raft can be effectively released from the array by the action of a needle inserted through the PDMS substrate. The use of a needle eliminates the necessity of building laser focal indicators on the pallet array, and also eliminates the possibility of laser damage to cells and rafts.

Arrays of micromolded concave rafts were fabricated on a PDMS plate. Cells fell in the microwells and attached to the surface of rafts so that the cells could be readily viewed with conventional microscopy. Single rafts were released by the action of a needle inserted through the PDMS plate. Upon release of a raft with an attached cell, the cell remained adherent to the underlying raft. The feasibility of collecting and then cloning the cell on the released raft was demonstrated. Cell isolation based on fluorescence and creation of a pure fluorescent cell line was demonstrated.

Materials and Methods

Materials.

SU-8 photoresist was purchased from MicroChem Corp. (Newton, Mass.). The Sylgard 184 silicone elastomer kit was purchased from Dow Corning (Midland Mich.). Gamma-butyrolactone, octyltrichlorosilane, propylene glycol monomethyl ether acetate, rhodamine B, glutaraldehyde, L-glutamine were obtained from Sigma-Aldrich (St. Louis, Mo.). EPON epoxy resin 1009F and 1002F (fusion solids) were purchased from Miller Stephenson Chemical Co. (Sylmar, Calif.). Dulbecco's Modified Eagle Medium (DMEM), fetal bovine serum (FBS), and penicillin/streptomycin were obtained from Invitrogen (Carlsbad, Calif.). Polycarbonate plates (12 inch×12 inch×0.25 inch) were purchased from McMaster-Carr (Los Angeles, Calif.). All other reagents were from Fisher Scientific (Pittsburgh, Pa.).

Fabrication of Mold.

The microwell array was fabricated by casting PDMS on a mold. The mold was fabricated by standard photolithography on a glass slide with 40-100 um thick SU-8 with an area of microstructures of 25.4 mm×25.4 mm. Glass slides were first rinsed with deionized water and ethanol to remove dust, and dried with a stream of nitrogen. The slides were then cleaned with the air plasma cleaner (Hayrick Plasma, Ithaca, N.Y.) for 3 min before use. SU-8 films of 50-μm thickness were obtained by spin-coating SU-8 photoresist (formulation 50) on the glass slides following the protocol provided by MicroChem Corp.[30] Briefly, approximately 2-3 mL of SU-8 was dispensed to the center of glass slides, and then the resist was spin-coated at 500 rpm for 10 s followed by 2000 rpm for 30 s on a WS-200-4NPP spin coater (Laurell Technologies Corp., North Wales, Pa.). The coated slides were baked on a hot plate at 65° C. for 6 min followed by a second bake at 95° C. for 20 min to remove organic solvent. To prepare SU-8 mold, the SU-8 film was exposed to UV light at a dose of 400 mJ/cm$^2$ through a photomask with the designed features using an Oriel collimated. UV source equipped with a 350 nm short pass filter (Omega Optical, Brattleboro, Vt.). The post-exposure baking was performed on a hot plate at 65° C. for 1 min followed by a second bake at 95° C. for 5 min. The SU-8 samples were then developed in SU-8 developer for 6 min, rinsed with 2-propanol, and dried by a stream of nitrogen. The mold is finally hard baked on a hotplate at 120° C. for 1 h. Fabrication of SU-8 molds of alternative thicknesses (20-100 him in this study) was performed using the same process, except that the appropriate time parameters for that thickness were substituted.[30]

Fabrication of PDMS Microwell Array.

The surface of the mold was treated to render it non-sticky to PDMS by spin coating 1 vol % octyltrichlorosilane in propylene glycol monomethyl ether acetate at 2000 rpm for 30 s, followed by baking at 120° C. hotplate for 10 min. PDMS prepolymer (10:1 mixture of base:curing-agent of Sylgard 184 kit) was spread on the mold, and degassed under vacuum to remove trapped air bubble. To control the thickness of PDMS to be around 200 μm, PDMS on the mold was spin-coated at 500 rpm for 30 s. PDMS was cured by baking the mold on 100° C. hotplate for 30 min. PDMS microwell array (FIG. 3A-i) was obtained by peeling it from the mold.

Micromolding of Rafts on the Microwell Array.

Figure 3:
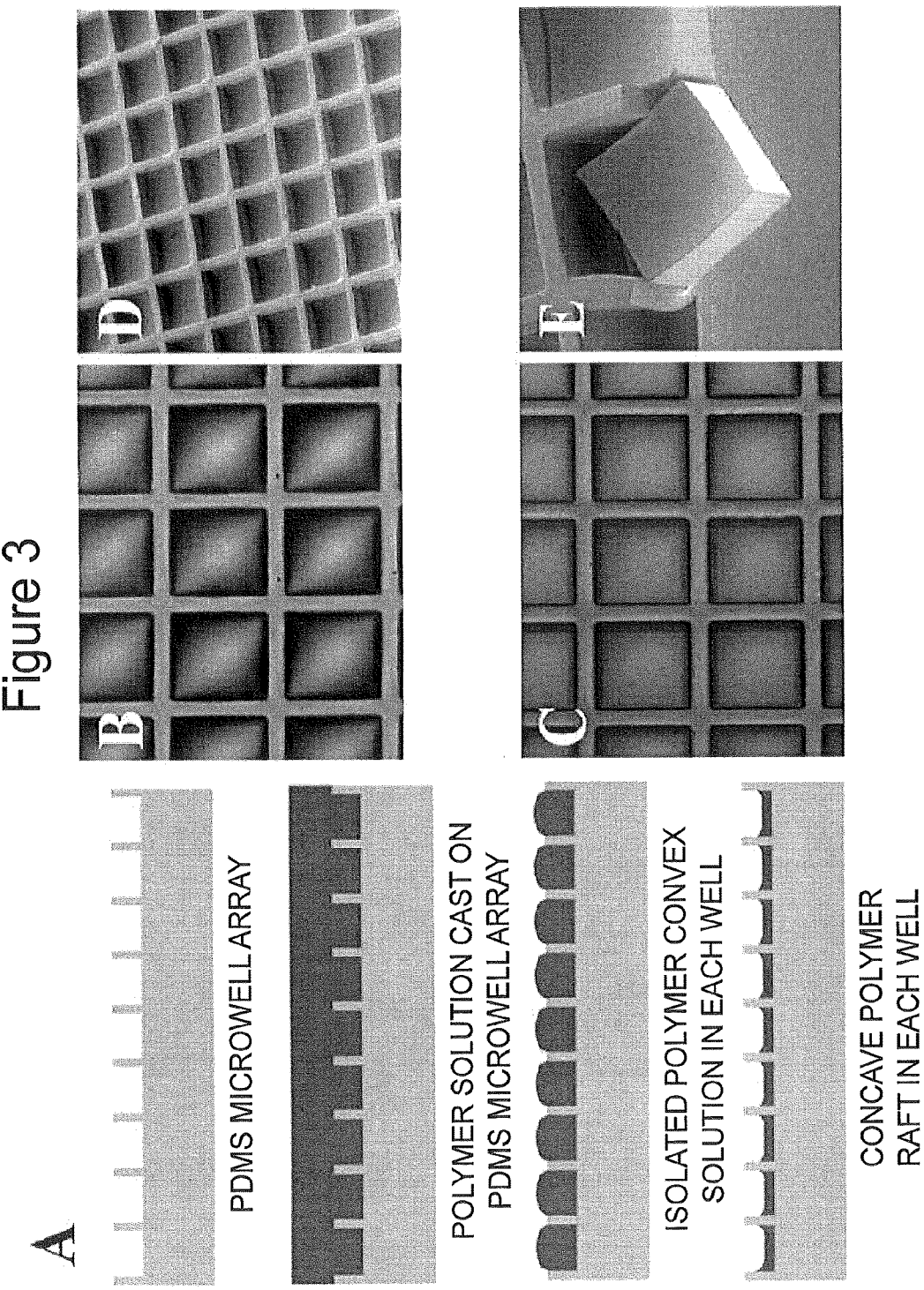
FIG. 3. Fabrication of microwell array bottomed with micromolded concave rafts. (A) Schematic of the fabrication process. (i) A polydimethylsiloxane (PDMS) microwell array was fabricated by standard molding process. (ii) A polymer solution was cast on the PDMS microwell array. (iii) Polymer solution flew from the array and resulted in isolated polymer convex solution in each well. (iv) Evaporation of solvent resulted in a concave polymer raft forming the base of each well. (B) Transmitted light micrograph of polymer convex solution in the array of microwells (100 μm square, 30 μm gap). (C) Transmitted light micrograph of polymer convex rafts in the microwell array after evaporation of solvent (100 μm square, 30 μm gap). (D) SEM image of a microwell array (175 μm square, 40 μm gap) with raft bases. (E) A close-up of an SEM image of a ruptured section showing that the concave raft has little adhesion to the PDMS well so that it can be easily detached.

A solution composed of 30 wt % 1009F epoxy resin in gamma-butyrolactone was prepared. An approximate amount of the solution was spread on microwell array (FIG. 3A-ii). The trapped air bubbles in microwells were removed by degassing under vacuum using an oil pump. The microwell array was then vertically hung on a rack using tape, and the excess polymer solution dewetted on the PDMS surface and slowly flew out of the microwell array. Thus each microwell was filled with a convex polymer solution (FIG. 3A-iii). The solvent (gamma-butyrolactone) in the polymer solution was evaporated by baking the microwell array in an oven at 95° C. for 3 h. The film was then further baked in a vacuum oven at 120° C. for 16 h to completely evaporate the solvent. At the same time 1009F epoxy resin was solidified by thermally induced epoxy ring-opening and condensation reactions.[31] With the evaporation of solvent, polymer in each microwell shrank and finally solidified at the bottom of the well into a concave raft (FIG. 3A-iv). The height of the raft was approximately 30% of the total height of the well.

Cell Culture on the Raft Array.

A plastic chamber (25.4 mm×25.4 mm×6.35 mm) was machined from a polycarbonate plate by a computer numerical controlled (CNC) machine. The plate of microwell array with detachable rafts was glued to the chamber by using PDMS and cured in an oven at 70° C. for 1 h. The array and the chamber were treated with air plasma cleaner for 5 min. The array was sprayed with 75% ethanol for sterilization, and then dried in a biosafety cabinet. 3 mL of phosphate buffered saline (PBS) was added into the chamber. To 'remove the trapped air bubbles inside the microwells, the plate was placed in a sterile vacuum desiccator (catalog #71236, Electron Microscopy Sciences, Hatfield, Pa.) and degassed for 20 min at room temperature inside the biosafety cabinet. The plate was then taken out of the desiccators, PBS buffer was aspirated, and a suspension of HeLa cells (10,000 cells) was added to the chamber. The cells were cultured on the array in DMEM supplemented with FBS (10%), and L-glutamine (584 mg/L) at 37° C. in a humidified, 5% CO2 atmosphere. Penicillin (100 units/mL) and streptomycin (100 μg/mL) were added to the media to inhibit bacterial growth. Immediately prior to use, the growth medium was removed from the cell chamber and replaced with PBS.

Release of Rafts by a Needle.

Figure 5:
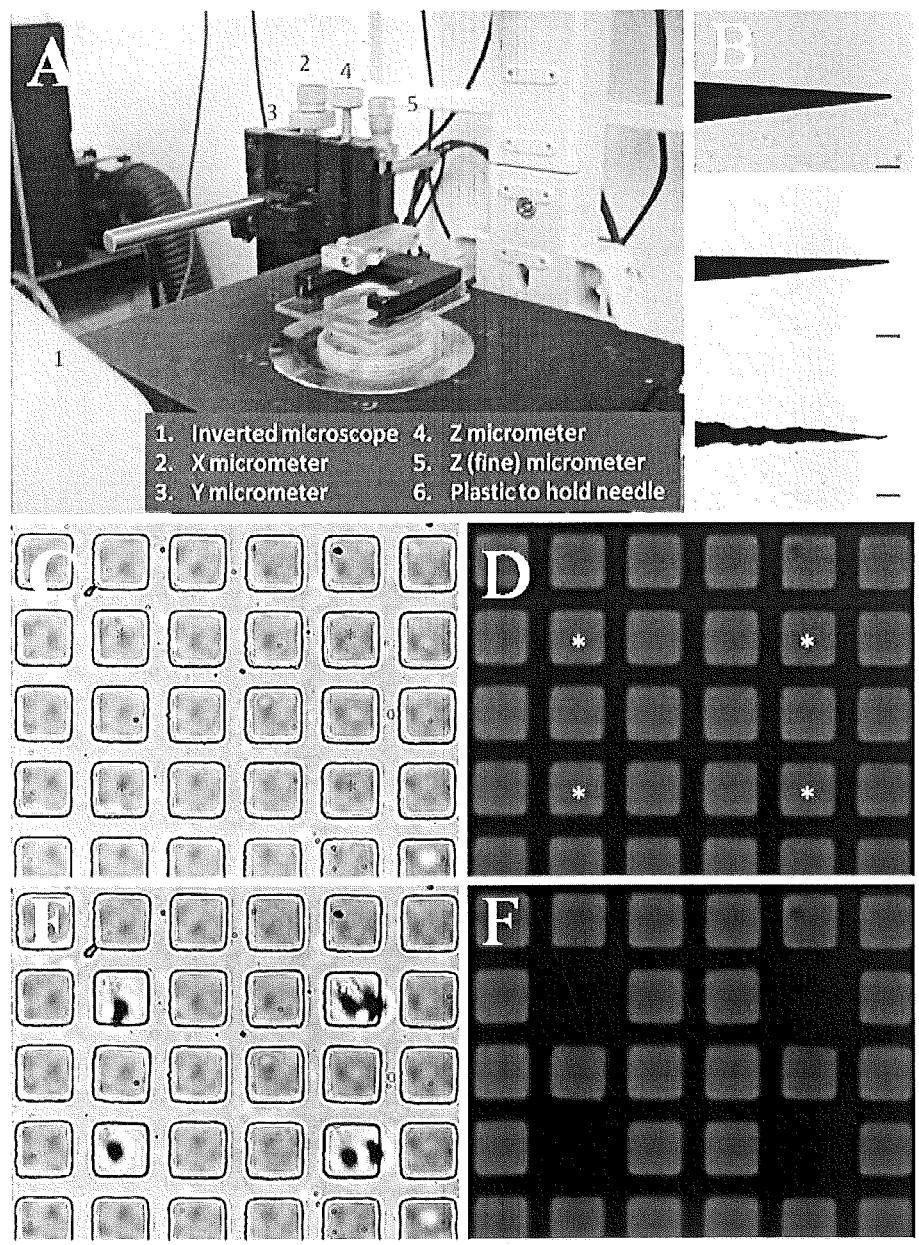
FIG. 5. Release of individual rafts from the array by needle release. (A) Experimental setup of the needle release system. The needle was fixed on a transparent polycarbonate block, and the position of the needle was controlled by an x-y-z manipulator. The manipulator was installed on the stage of an inverted microscope. (B) Micrographs of needles used for release (from top to bottom): tungsten carbide, anodized steel, tungsten. The scale bar is 100 μm. (C) Shown is an array of square molded rafts (50 μm side, 15 um height, 25 μm spacing). The rafts marked with an asterisk were released as shown in (E). (D) The fluorescence image of the raft array in (C). The polymer solution used to form the rafts was mixed with 100 ppm of rhodamine B in order to visualize the rafts by fluorescence microscopy. (E) The four rafts marked in (C) were sequentially released with a needle. (F) The fluorescence image of the raft array in (E). After release, the four rafts dropped from the array into the collection dish.

The concave raft composed of 1009F epoxy resin was readily dislodged from the well by the action of a needle inserted through the PDMS (FIG. 5). Three type of needles were tested (FIG. 5B): the anodized steel needles (150 vim base diameter, 17.5 μm tip diameter) and tungsten needles (125 μm base diameter, 1 μm tip diameter) were purchased from Fine Science Tools (Foster City, Calif.), and tungsten carbide needles (508 μm base diameter, tip angle=10°, tip radius=12.7 μm) were purchased from Semprex Corporation (Campbell, Calif.). A needle was inserted into a small PDMS plate (length×width×height=25 mm×25 mm×0 3 mm), and the PDMS plate was self-stuck to a polycarbonate plate (length×width×height=76.2 mm×76.2 mm×3.2 mm) having a cavity of (length×width×height=25.4 mm×25.4 mm×3.2 mm). A micromanipulator was installed on the stage of an inverted fluorescence microscope (TE300, Nikon). Then the polycarbonate plate with fixed needle was attached to the micromanipulator. The needle was moved to the center of imaging field by the x- and y-direction micrometers. The needle was lowered to punch through the PDMS by controlling the z-direction micrometer (FIG. 5A).

Cell Collection after Needle Release of Raft.

A collection chamber (40 mm×40 mm×6.35 mm) was machined from a polycarbonate plate by a CNC machine, and its bottom was glued with a glass plate. Prior to needle release, the microwell array was rinsed with fresh culture medium to remove nonadherent and dead cells. Then 4 mL of fresh culture medium was added to the cell culture chamber, so that the liquid was close to overflow and formed a convex surface. The collection plate was placed directly above the cell culture chamber, and the excess liquid squeezed out. In this manner an enclosed compartment was formed between microwell array and collection plate filled with culture medium. Then the assembly was inverted and placed on the microscope stage. The selected cells were released by the needle by detaching the rafts to which they were attached. The raft carried the cells to the collection plate by gravity force. The collection plate and microwell array were separated in a sterile environment. The collection plate containing the released cells/rafts was placed into a polystyrene Petri dish and transferred to a standard tissue culture incubator. The growth of the collected cells was observed over time by transmitted light microscopy.

Characterization of Fluorescence with Standard Microscopy Filter Sets.

1002F photoresist was formulated according to a previous publication.[24] Films of SU-8 photoresist (50 tm thickness), 1002F photoresist (50 um thickness), 1009F resin (50 μm thickness), PDMS (120 um thickness) were prepared on glass slides by spin coating at an approximate spin rate, and baked in an oven at 95° C. for 1 h to remove solvent or to cure. The SU-8 and 1002F film were exposed to UV at a dose of 400 and 800 mJ respectively, and baked at 95° C. for 10 to finish photoinduced crosslinking reaction. Finally, all four types of films were baked at 120° C. for 2 h. The fluorescence of the films were examined by a Nikon Eclipse TE300 inverted fluorescent microscope equipped with three fluorescent filter sets: a fluorescein filter set (B-2A; Nikon Instruments; excitation filter 450-490 nm, dichroic 500 nm long pass, emission 520 nm long pass); a TRITC filter set (G-2E; Nikon Instruments; excitation filter 528-553 nm dichroic 565 nm long pass, emission 590-650 nm); and a Cy5 filter set (41008; Chroma Technology, Rockingham, Vt.; excitation filter 590-650 nm, dichroic 660-nm long pass, emission 665-740 nm). Data were collected by a cooled CCD camera (Photometrix Cool Snap; Roper Scientific, Tucson, Ariz.) using Metafluor Software (Molecular Devices, Sunnyvale, Calif.).

Fluorescence Microscopy.

Transillumination and fluorescence microscopy were performed using an inverted microscope (TE300, Nikon). Imaging of GFP-expressing cells was performed using a standard fluorescein filter set.

Scanning Electron Microscopy (SEM) of Cells.

Cells plated on microwell arrays were rinsed gently with PBS and then fixed with 2.5 wt % glutaraldehyde in PBS for 30 min. This sample was washed with PBS, and dehydrated with a series of ethanol/water mixtures of increasing ethanol concentration (30%, 40%, 50%, 60%, 70%, 80%, 90%, and 100% ethanol, 10 min in each mixture). The fixed cells were observed by SEM (FEI Quanta 200 ESEM, FEI Company).

Results and Discussion

Fabrication of Microwell Array with Detachable Bases.

Microwell arrays with controlled depth and dimension were fabricated by casting PDMS against a mold. This molding process has been generally used in fabricating microfluidic channels and microdevices.[32, 33] The fabricated PDMS microwell array has been used to pattern cells for a variety of applications including imaging cytometry,[34] hybridoma selection,[35] microenvironment for stem cell research,[36, 37] etc. PDMS microwell array has been combined with optical tweezers or micropipette to isolate the selected non-adherent cells.[35, 38, 39] The mold was fabricated by using SU-8 photoresist and the standard photolithography process. The microwell arrays with density of over 600-5000 wells/cm-2 are used for the current experiments, and the dimension of wells is in the range of 30-300 μm (FIG. 3A-i).

A filling-dewetting process was used to mold pallets in the microwells (FIG. 3A). We observed that a polymer solution composed of 30 wt % of EPON epoxy 1009F resin in gamma-butyrolactone does not wet PDMS. When a drop of the solution was added to a PDMS plate and the plate was tilted, the solution gradually traveled out of the PDMS surface without leaving any residue. This dewetting phenomenon is caused by their mismatched surface tension. PDMS has a surface tension of 16-21 dyne/cm, while gamma-butyrolactone is a polar solvent with a relatively high surface tension of 40 dyne/cm, and EPON epoxy resin has a surface tension of 44-49 dyne/cm. The 1009F polymer solution was added the PDMS microwell array, and vacuum was used to remove the trapped air bubble inside each well (FIG. 3A-ii). When the PDMS is tilted or hung vertically, the polymer solution slowly drained off the PDMS surface due to dewetting, leaving each well filled with polymer solution. As a result, an array of microwells individually filled with polymer solution was achieved on the PDMS plate (FIG. 3A-iii). The polymer solution was found to be convex in each well (FIG. 4B). The plate was then baked at elevated temperature to evaporate the solvent. The evaporation caused shrinkage of the polymer. A concave polymer pallet is generated inside each well at the end of solvent evaporation (FIG. 3A-iv, FIG. 3C). The concave shape is caused by the mismatched surface tension between PDMS and 1009F resin/gamma-butyrolactone during solvent evaporation. The thickness of the pallet can be adjusted by the concentration of epoxy resin in solvent. By using 30 wt % resin concentration, the height of pallet is approximately ⅓ of the depth of the well. Gamma-butyrolactone was found to be compatible with PDMS with negligible swelling.[40] 1009F resin was used due to its high melting point ($T_m$=130-140° C.) and its low autofluorescence. FIG. 3D shows the microwell array bottomed with molded rafts. The concave shape of each raft is clearly shown in a ruptured section (FIG. 3E). The raft has poor adhesion to the PDMS well so that it can be easily detached.

In the filling-dewetting process, the microwell array was used as the template for molding of pallets. The micromolding process does not require any microfabrication tool and a cleanroom facility; a small laminar flow bench is enough for the whole micromolding process. A mold for fabricating PDMS microwell array can be obtained from a microfabrication foundry service. As a result, the fabrication process becomes extremely simple and inexpensive after obtaining a mold.

Micromolding is a versatile process to fabricate rafts. It requires a simple polymer solution composed of resin and solvent, and it does not require inclusion of photocatalyst. In contrast, photocatalyst is an indispensable component of the photoresist for fabricating pallets using photolithography. On the other hand, the polymer solution can include other components (e.g. magnetic particles, color or fluorescent dye, pore generator, etc.), so that functional rafts (e.g. magnetic, color-coded or fluorescent, porous, etc) can be easily molded. It is always difficult to fabricate functional pallets by photolithography, since the functional component usually interferes with or blocks the UV light needed for development.

Autofluorescence.

Figure 4:
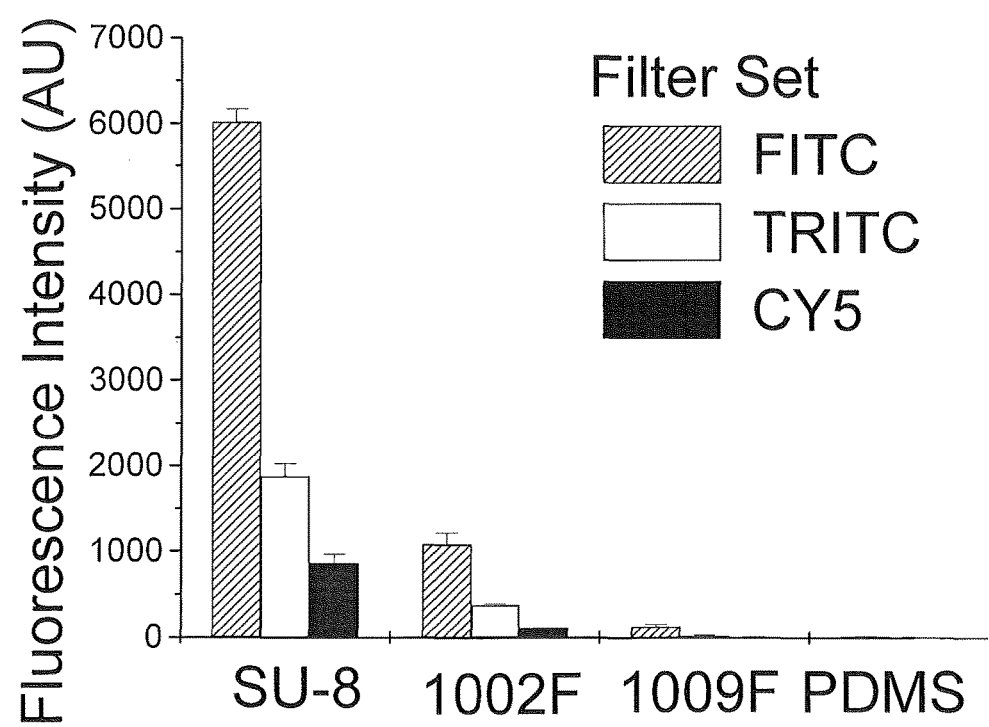
FIG. 4. Fluorescence of films of SU-8 photoresist (50-μm thickness), 1002F photoresist (50-μm thickness), 1009F resin (50-μm thickness), and PDMS (120-μm thickness) using common microscopy filter sets. Films of varying thickness were coated onto glass slides. The fluorescence intensity of the films was measured using a fluorescein filter set (hatched bars), a TRITC filter set (white bars), or a Cy5 filter set (black bars).

Fluorescence-based assays are important tools for cell selection. SU-8 and 1002F, the photoresist from which the pallets are constructed by photolithography, has strong autofluorescence in the range of 480-520 nm.[22, 24] This wavelength range unfortunately coincides with the wavelength of the most frequently used dyes (e.g. FITC, Oregon green, Alexa Fluor 488, etc) for fluorescence imaging. 1002F photoresist has a lower level of autofluorescence than SU-8. The SU-8 or 1002F photoresist contains about 5 wt % photoinitiator, triarylsulfonium hexafluoroantimonate. The autofluorescence comes from the photodecomposition by-products which have conjugated structure.[41] Using the micromolding method, the raft is composed of only 1009F resin, and as a result the autofluorescence is very low. To determine the level of auto-fluorescence, thin films of SU-8 photoresist, 1002F photoresist, 1009F resin and PDMS were spin coated on glass slides, and their fluorescence, intensity was obtained with commonly used filter sets in fluorescence microscopy (FIG. 4). The thickness of film was 50 µm, except that PDMS has a film thickness of 120 um and it is shown for comparison. Under FITC filter set, the autofluorescence of 1009F resin is only 2% of that of SU-8 photoresist, and 12% of that of 1002F photoresist. The autofluorescence of 1009F resin is slightly higher than that of PDMS, which is generally considered one of the lowest autofluorescence polymers.[42] Under TRITC and CY5 filter sets, the autofluorescence of 1009F resin is almost negligible. Compared with SU-8 and 1002F photoresist, the reduced autofluorescence of 1009F resin is due to the absence of photocatalyst. The reduced autofluorescence of molded pallets is particularly valuable for highly sensitive measurements.

Release of Individual Rafts from a Large Array with a Needle.

Figure 7:
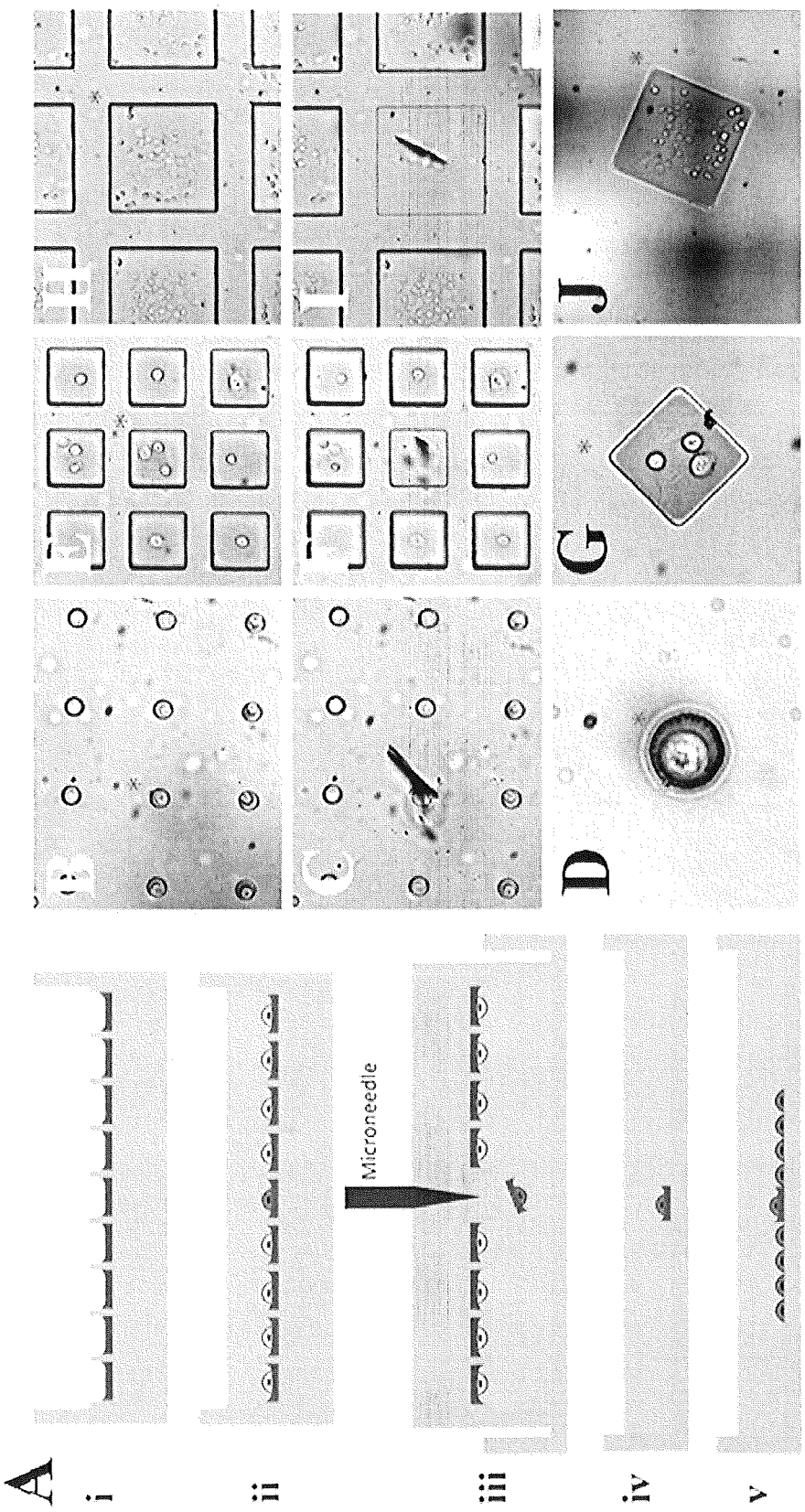
FIG. 7. Needle-based release of adherent cells grown on the concave rafts from the microwell array. (A) Schematic of the release process. (i) An array of microwells with detachable rafts as their base was assembled on a cassette and the surface was oxidized with air plasma. (ii) Cells were plated on the array and allowed to attach to the rafts. iii) The chamber containing the array was filled with medium, covered by a collection chamber and the assembly was inverted. The cell of interest (depicted in green) was separated from the array by dislodging the raft to which it was attached using a needle. (iv) The raft transported the isolated cell to a new culture dish. (v) The isolated cell continued to grow. Transmitted light micrographs showing the selected HeLa cells (marked with an asterisk) were released from the array by a needle. (B-D) A single HeLa cell was isolated with a 30 μm raft. (E-G) Five HeLa cells were isolated with a 100 μm raft. (F-J) A colony of HeLa cells (number of cells >100) was isolated with a 300 μm raft. (B), (E) and (H) are images before needle penetration. (C), (F) and (I) are images after needle penetration, showing the targeted rafts were released without disturbing neighboring rafts. (D), (G) and (J) are images showing the targeted cells were transported to the collection dishes by the rafts and that the released rafts remained intact.

The micromolded rafts are seated at the bottom of PDMS microwells. Although rafts have shown poor adhesion with PDMS (FIG. 3E), they are not easily detached from the array since they are surrounded by PDMS wells. The selected raft can be detached from the array simply by the mechanical action of a needle pushed through the PDMS from the backside. PDMS is a flexible material, and a needle can easily penetrate a PDMS film of 200 um thickness. FIG. 5A shows the needle system built on an inverted microscope. The needle was attached on the transparent plastic plate, and its movement at x, y, and z direction was controlled precisely by a micromanipulator. The needle was moved to the center of field of view by x and y micrometers. The raft to be released was the moved to the spot the needle would penetrate. The penetration depth was controlled by lowering the needle by z micrometer. Depending on the size of raft, a variety of needles can be used. FIG. 5B shows three types of needles used for releasing rafts. The tungsten carbide needle (top) with a tip diameter of 12.7 µm and the anodized steel needle (middle) with a tip diameter of 17.5 µm are suitable for releasing big rafts, while the tungsten needle (bottom) with a tip diameter of 1 µm is suitable for releasing small rafts. To demonstrate the release of individual rafts, a large array composed of 17,780 rafts/cm$^2$ (50 µm size, 25 µm gap) was used. The raft was doped with 100 ppm of rhodamine B so that the detachment of rafts from the array could be clearly visualized by fluorescence microscopy. The selected rafts (marked with asterisk) were released by inserting the needle through the PDMS and punching the raft out of the microwell. The release of rafts was confirmed by watching the raft float away from the microwell array under the microscope. Most of the rafts were released from the array by only one punching action (81%, N-140). Sometimes additional penetrations were required before release was accomplished: two (14%, N=140), three (4%, N=140), or four (1%, N=140). The penetration site could be visualized in the PDMS after withdrawal of the needle (FIG. 5E). To confirm the release of rafts, rhodamine B doped rafts were observed under fluorescence microscopy before and after penetration of the PDMS with the needle (FIG. 5D,F). The images clearly show the four selected rafts were released without disturbing neighboring rafts. In this experiment, 100% (N=140) of targeted rafts were released and 0% of adjacent rafts were detached. Multiple rafts in an array could be released by moving the microscope stage to sequentially place rafts under the point of needle penetration. Larger rafts are more easily released from the array. The smallest rafts tested had a diameter of 30 µm (FIG. 7B,C,D). For small rafts, a gap of at least 25 µm prevented adjacent rafts from being disturbed by the needle release action. Since the rafts were individually addressable and releasable with the needle, the rafts were suitable candidates for the array-based scanning and cloning of adherent, mammalian cells.

Cell Culture on Microwell Array with Detachable Rafts.

Figure 6:
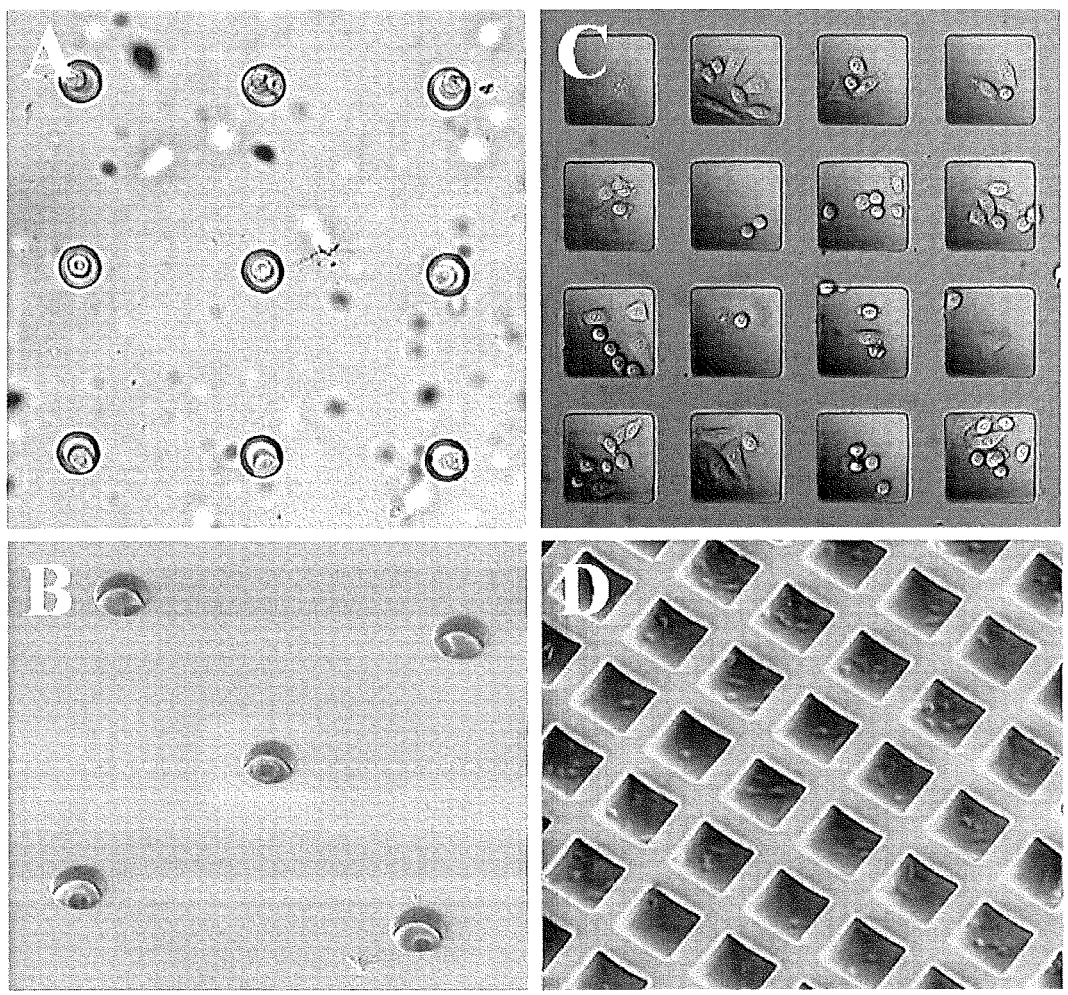
FIG. 6. Patterning of cells on the 'microwell array bottomed with detachable rafts. (A) and (B) Single HeLa cells were patterned on a 30 um microwell array (15 μm depth, inter-well gap of 120 μm; height of pallet: 9 μm). (C) and (D) A multiple of HeLa cells were patterned on a 100 μm microwell array (50 μm depth, inter-well gap of 50 μm; height of base: 15 μm). (A) and (C) are transmitted light micrograph images, and (B) and (D) are SEM images.

To determine if rafts surrounded by a PDMS well could be used to create a cell-based array, arrays were oxidized by plasma cleaner for 5 min to provide a surface suitable for cell attachment. HeLa cells were plated on the arrays. Most cells fell into the wells by gravity, and settled near the center of rafts due to the concave surface shape of the rafts. Twenty minutes after cell plating, the array was gently rinsed with fresh medium to remove the cells that did not fall into the wells. 30 µm rafts were used to create an array of single cells per raft (FIG. 6A), and 100 µm rafts were used to create an array of multiple cells per raft (FIG. 6C). The arrays were examined by microscopy after 6 h. 95% of cells (N=500 cells) were located inside the well and attached to the pallets. SEM images (FIG. 6B,D) corroborated these findings.

Release of Individual Rafts with Cells.

To determine the feasibility of releasing rafts with living cells, the pallets with cells on their surface were released using a needle as described above (FIG. 7Aiii). To isolate single cells, an array of 30 µm rafts was used. The selected single cell (marked with asterisk) was separated from the array by detaching the raft on which it was attached. The release process is shown in FIG. 7B, C, D. After release, the cell stayed attached to the raft and was unharmed by the process. To isolate a small colony of cells (5-10 cells), an array of 100 µm rafts was used (FIG. 7E, F, G). To isolate a larger colony of cells (>30 cells), an array of 300 µm rafts was used (FIG. 7H, I, J).

Proliferation of Single Cells from Released Rafts.

Figure 8:
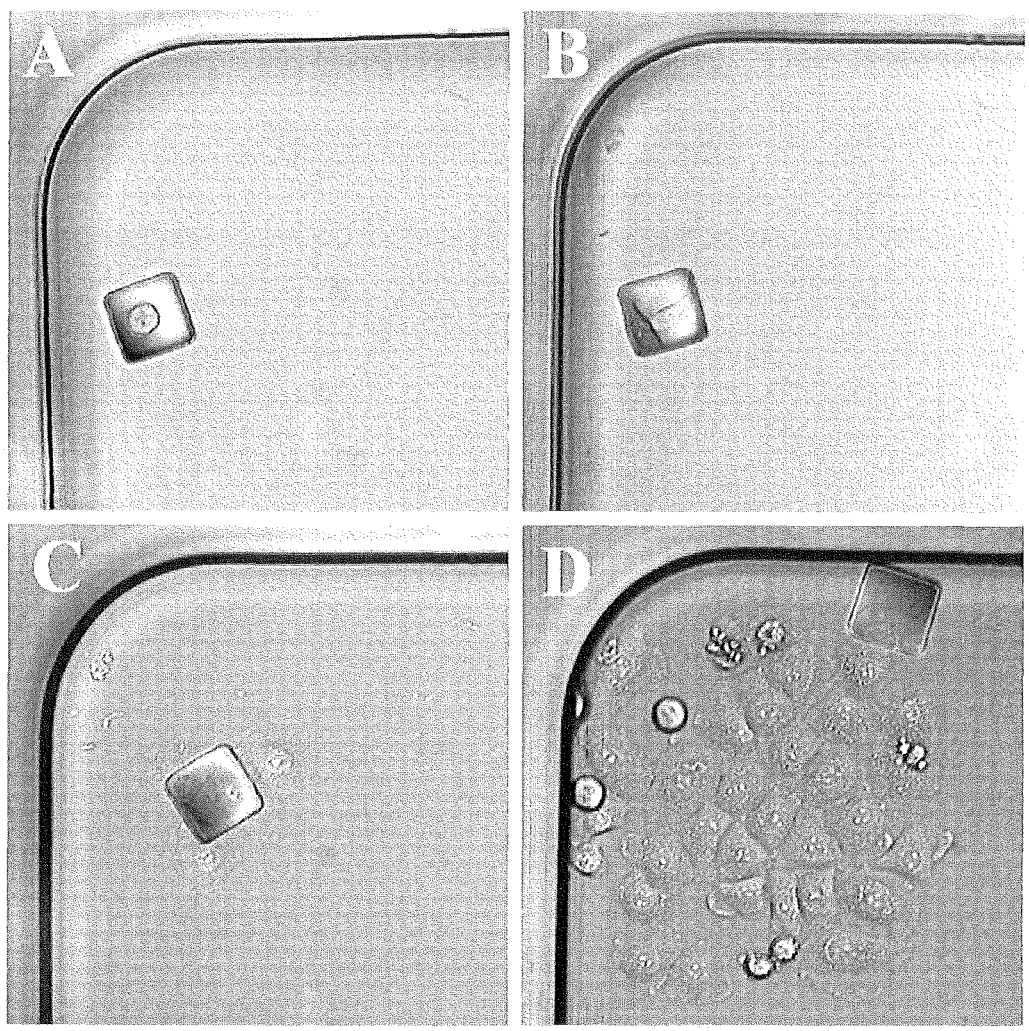
FIG. 8. Proliferation of single cells after needle release. The released single HeLa cell on a raft (length×width×depth=50 μm×50 μm×15 μm) was collected, and imaged at 0 h (A), 24 h (B), 48 (h) (C) and 144 (h) (D) after the initiation of culture.

To determine the feasibility of collecting single cells for culture and expansion, rafts (length×width×depth=50 µm×50×15 µm) with single HeLa cells were released, collected, and placed into a culture dish. The cells were imaged by microscopy within an hour of collection and then at varying times thereafter. At one hour after collection, the HeLa cell remained on the raft top (FIG. 8A). By 24 h after collection, single cells divided into two daughter cells (FIG. 8B). The cells had migrated from the rafts onto the adjacent surface by 48 h (FIG. 8C). By 144 h, the single cell had expanded into a small colony to create a clonal population from the original single cell. Of the released single HeLa cells 95% (N=40) proliferated into colonies. These data demonstrate the feasibility of collecting living, single cells from the raft array and producing clonal colonies. In similar experiments using rafts containing a colony of HeLa cells (number of cells >3), the proliferation rate was 100% (N=10).

Cell Sorting Based on Fluorescence.

Figure 9:
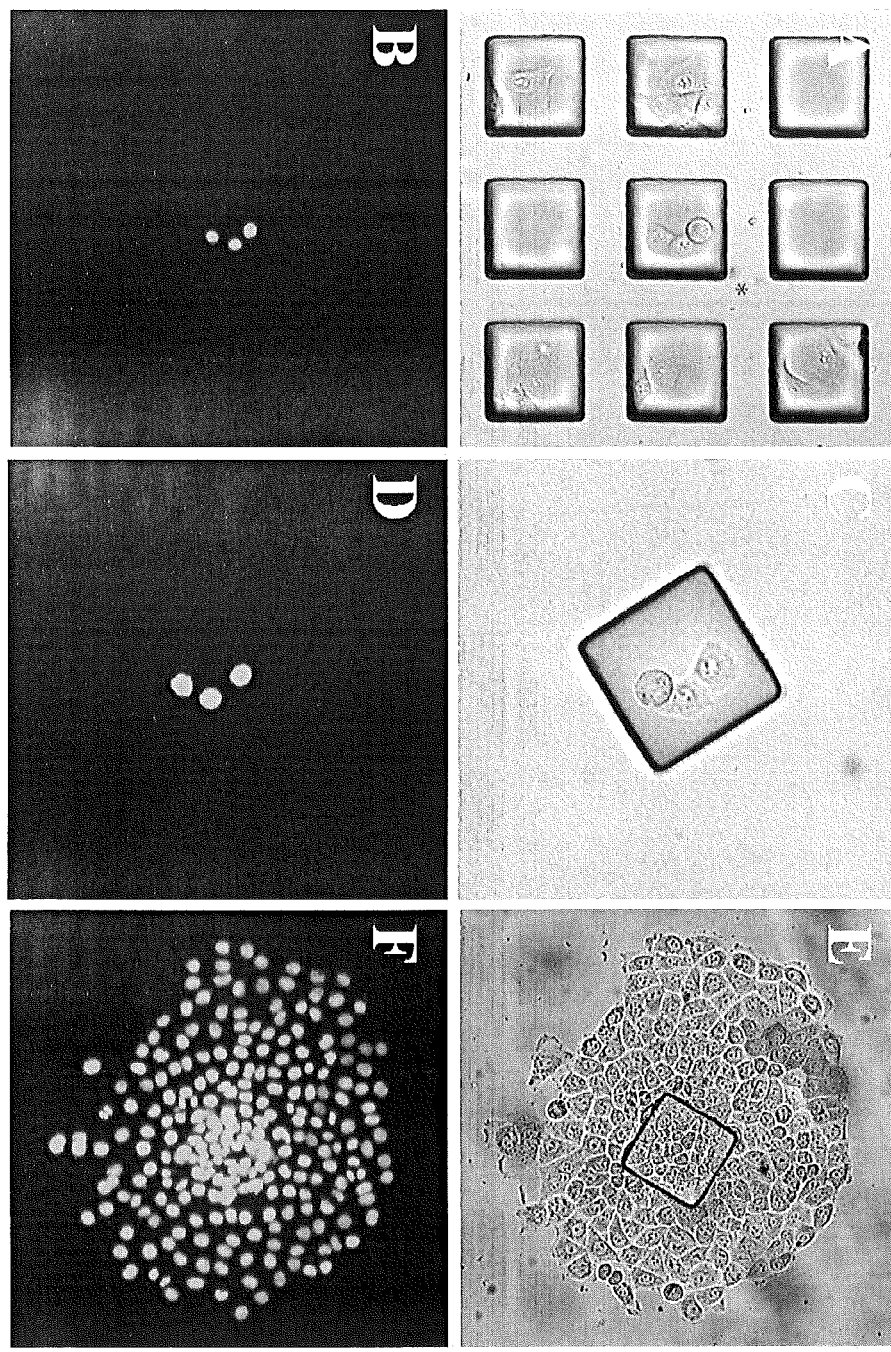
FIG. 9. Isolation of colonies of eGFP-expressing cells. (A) Transmitted light image of HeLa cells on an array. (B) Fluorescent image of the cells shown in (A). (C) Raft with eGFP-expressing cells was released from the array. Shown is a transmitted light image immediately after collection. (D) Shown is the fluorescence image of the cells and raft shown in (C). (E) Shown is the same raft in collection well shown in (C) 6 days after collection. The cells have expanded into a colony of >200 cells. (F) The fluorescence image of the raft and collection well shown in (E).

To demonstrate cell sorting based on fluorescence, a HeLa cell line stably transfected with the enhanced green fluorescent protein (eGFP) fused to the histone-H1 protein was used. Histone-H1 is tightly associated with cellular DNA so that transfected cells display green fluorescence localized to their nuclei. Wild-type HeLa cells were mixed with the eGFP-histone-H1 expressing cells at a ratio of 500:1, respectively. The cells were then plated on an array of molded rafts (length×width×depth=100 µm×100 µm×15 µm) at limiting dilution to yield 1 cell/pallet: i.e. 28,000 cells were plated on the array composed of 28,000 wells/rafts. The array was imaged by microscopy (transmitted light and fluorescence). Pallets with fluorescent cells were easily visualized amongst rafts containing nonfluorescent cells (FIGS. 9A and 9B). Under these conditions, no background fluorescence from the rafts and PDMS was detectible. After 48 h, a proportion of rafts on the array contained 3-5 fluorescent cells, which were the daughter cells from the single parental cells originally plated on the raft array. To demonstrate sorting of these clonal colonies, individual rafts containing fluorescent colonies were selected, released, collected, and placed in culture (FIGS. 9C and 9D). Expansion of these fluorescent colonies for 6 days yielded clonal populations of cells expressing the fusion protein (FIGS. 9E and 9F). These experiments demonstrate the ability to sort colonies of cells based on whether the individual cells retain the properties of the parental cell. This selection strategy may find utility in the molecular engineering of cells or the development of cell lines, for example, stem cells.

Comparison with the Currently Used Cell Sorting Methods.

Current methods for cell sorting of adherent cells rely on either re-suspending adherent cells so that they may be used in a flow cytometer, or the use of a time consuming process called "limiting dilution". Suspending cells is not desired because the suspending process damages the cells and places them in an unnatural state (not adhered to a surface). This process also causes the loss of morphologic features of the normally adherent cell. Limiting dilution is a time consuming and laborious assay, resulting in only an enriched sample of target cells. Sorting by flow cytometry is expensive as the instrument generally retails for several hundred thousand dollars and requires a trained and dedicated technician. As a result, shared cell sorting facilities are established in research universities and institutes. Operating, maintaining, and staffing a sorting facility is an expensive undertaking.

The micromolded raft array technology has a number of unique advantages over other cell sorting methods. First, in the raft array technology, individual cells of interest are identified then isolated by detaching the structure that supports the cells. Each cell remains fixed on the solid surface at all times. This simplicity and robustness allows one to rapidly isolate adherent cells without the need to re-suspend them, and without the need to perform a limiting dilution. In a single step, a researcher can quickly scan tens of thousands of cells and collect one or several cells from the initial population. Cells experience no stresses and are completely viable for further growth and expansion. Second, the cells can be rescanned multiple times, as the cells are completely unharmed in the scanning and isolation process, making this technology an extremely attractive alternative to flow sorting when adherent cell assays are desired. Third, cells can be separated based on new sorting criteria that other methods cannot do, for example, cell morphology, cell growth rate, and cell secretion. No other company (including industry leaders) offers a similar product. Finally, raft array technology is extremely simple and it does not rely on any sophisticated equipment, making it affordable for any biology laboratory. It provides an inexpensive yet efficient method for biologists to perform cell sorting and creation of cell lines in their laboratory. The technology is especially valuable for sorting of very small samples (1,000-100,000 cells), such as those obtained from animal models or biopsy specimens. The viability after sorting (whether cells are alive and able to grow) remains extremely high—well over 90% of sorted cells survive the sorting process by this method, unlike other methods where many if not most cells die after sorting. This means that stem cells and other primary cells taken directly from a tissue sample can be effectively isolated in the laboratory. The micromolded pallet array technology creates the possibility of opening an entire market of adherent cell sorting.

EXAMPLE 2

Coating Microraft Arrays with Biologically Active Molecules

1. Coating with Extracellular Matrices to Enhance Cell Attachment.

Figure 10:
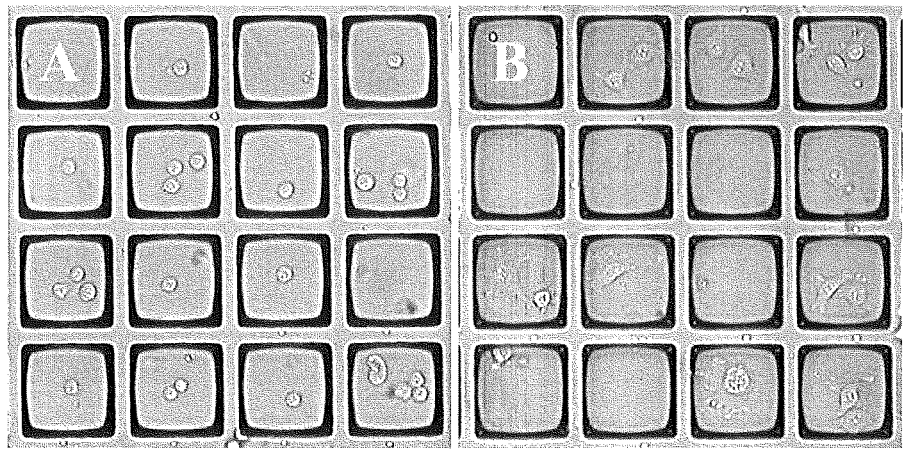
FIG. 10. Brightfield images showing attachment of HeLa cells on the microraft array 2 h after cell plating. (A) No ECM coating. (B) ECM coating (collagen, 100 µg/mL for 1 h). Raft material is poly(styrene-co-acrylic acid) (PS-AA). Raft size is 100 µm. Inter-raft gap is 20 µm.

Extracellular matrices (ECMs), such as collagen, gelatin, laminin and fibroncetin, can be coated on the microraft surface to enhance cell attachment. As the first example, a microraft array was coated with 100 µm/mL, collagen (type I from rat tail) for 1 h. HeLa cells attached quickly to the microrafts in 2 h (FIG. 10B). As a control, cells didn't attach to the non-coated array at the 2 h time point (FIG. 10A), although they did adhere and spread after 6 h.

Figure 11:
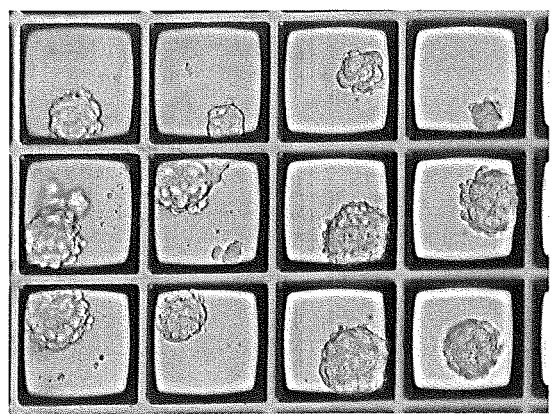
FIG. 11. Culture of mouse embryonic stem cell on the raft array. The array was coated with Matrigel (1/100 dilution with medium) for 30 min. Raft material is poly(styrene-co-acrylic acid) (PS-AA). Raft size is 200 µm. Inter-raft gap is 20 µm.

As a second example, in-vitro culture of stem cells generally requires supplying with ECMs to mimic in-vivo environment for self renewal. Matrigel can be coated on the microraft array for culturing stem cells. FIG. 11 shows mouse embryonic stem cell line ES129 cultured on the array at 50 h in the presence of leukemia inhibitory factor (LIF). The array was coated with Matrigel prior to plating the stem cells. The rafts of 200 µm size provided a suitable environment so that the stem cells renewed themselves and were maintained in the undifferentiated state.

2. Spotting with Biological Reagents for Screening Purposes.

Figure 12:
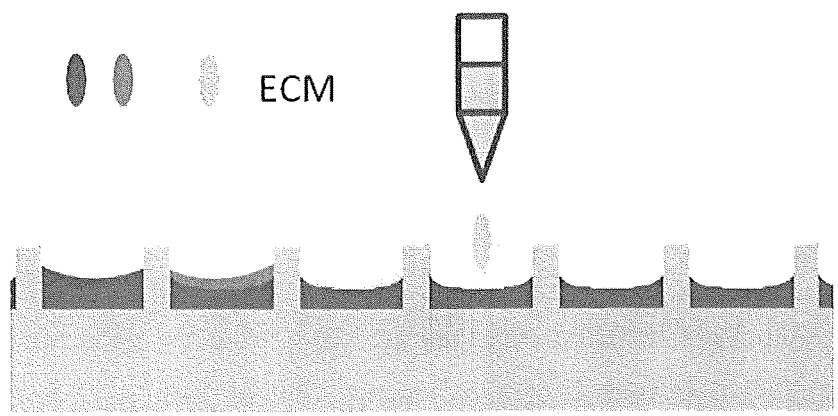
FIG. 12. Scheme of individually spotting different types or different mixing ratios of biological reagents on the microraft arrays before or after cell plating. The droplet could also contain a cell in suspension within the reagent and deposited on a particular raft after which the cell could be followed over time to assess response such as growth, differentiation or other property.

For screening purposes, the microraft array could be spotted with different types of biological reagents. A number of products are available for spotting liquid on the surface, e.g. ink jets or nano-pipettes. For example, the Nano eNabler™ system is a highly flexible molecular printer that can dispense minute volumes (1-30 µm sample droplet) of liquid at defined positions to create patterns of spots with high spatial accuracy (BioForce Nanosciences, Inc., 1615 Golden Aspen Drive, Suite 101, Ames, Iowa 50010 USA). Rafts are created in a microwell providing surrounding walls, making it ideal for spotting with ECMs or any other biological reagents (drugs, antibodies, growth factors, DNA plasmid etc.). Drops of reagent can be individually dispensed into the microwells (FIG. 12). Cells can then be plated on the array and the cells-reagent interactions can be quickly screened. Additionally, the cells with desirable interactions can be isolated from the array for further study. A very large number of rafts can be created on the array, e.g. 1 inch×1 inch array contains 45,000 rafts (100 µm size). Many types of reagents or many different mixing ratios can be spotted on the array; therefore, the microraft array provides a platform for studying cell-reagent interaction.

Instructions for Use of Microraft Array

1. Technical Data for Microraft Array

Chamber dimension: 25 mm (length)×25 mm (width)×5 mm (height), total volume 3125 $mm^3$ » 3.1 ml. Array dimension: 25 mm (length)×25 mm (width)=625 $mm^2$.

2. Microraft Specification

TABLE 1

| Size of Raft | height | length | width | Inter-raft space | Raft surface area | Total number on the array |
|---|---|---|---|---|---|---|
| 200 um | 30 um | 200 μm | 200 μm | 20 μm | 0.04 mm² | 12,910 |
| 100 um | 20 urn | 100 μm | 100 μm | 20 μm | 0.01 mm² | 43.401 |

3. Reagents
Cell culture medium appropriate for the cell type used
100% ethanol
Sterile phosphate buffered saline (PBS)
0.1% gelatin solution (diluted from 2% gelatin [Sigma Aldrich G1393] with PBS)

4. Protocol for Use. Note: All Steps Performed in a Laminar Flow Hood

1. The array has been sterilized and packaged in a sterile pouch. Open the pouch. Place the array in a petri dish.
2. Add 2 mL 100% ethanol to the array. Wait 3 min This purpose of this step is to eliminate air bubbles that may trapped in the microwells. You can check the array under microscope to make sure all air bubbles are gone.
3. Tilt the cassette slightly to the side and aspirate the ethanol.
4. Add 2 mL PBS to the array. Aspirate PBS.
5. Repeat 4 for additional four times. The purpose is to get rid of ethanol residue.
6. Add 2 mL gelatin solution to the array, and incubate for 10 min at room temperature. Aspirate gelatin solution.
7. Plate 2 ml of cell suspension per chamber.
8. Incubate cassettes at 37 C incubator
9. Monitor cell adhesion by microscopy.

General Consideration of Cell Numbers Per Array

The plating density for a particular cell line will depend upon the array used and optimal density for cell growth. A general guideline for a total number of cells to be plated to obtain a single cell/raft condition is to plate about ½ of the number of rafts on the array (Table 2). However, cell density can be titrated for optimal results.

TABLE 2

| Size of Raft | Total # of rafts per array | Array cell growth area | Total volume for plating | Suggested total cell # per array | Suggested final concentration |
|---|---|---|---|---|---|
| 200 um | 12,910 | 5.16 cm² | 2 mL | 6,400 | 3,200 cells/mL |
| 100 um | 43.400 | 4.34 cm² | 2 mL | 21,700 | 10,800 cells/mL |

Culture of Stem Cells on Raft Array Coated with Matrigel™ Basement Membrane Matrix.

Raft array: 200 um×200 um (L×W) wells. There are 13,000 wells on the entire array. All steps performed in a laminar flow hood 1. The array has been sterilized and packaged in a sterile pouch. Open the pouch. Place the array in a petri dish.
2. Add 2 mL 70% ethanol to the array. Wait 3 min. The purpose of this step is to eliminate air bubbles that may trapped in the microwells. You can check the array under microscope to make sure all air bubbles are gone.
3. Tilt the cassette slightly to the side and aspirate the ethanol.
4. Add 2 mL sterile phosphate-buffered saline (PBS) to the array. Aspirate PBS.
5. Repeat step 4 for additional four times. The purpose is to get rid of ethanol residue.
6. Dilute 20 uL gelatin with 2 mL cold medium. Add 2 mL diluted gelatin solution to the array. The array is placed in a 37 C incubator for 30 min.
7. Aspirate gelatin solution.
8. Plate 2 ml of cell suspension per chamber. Total cell=10,000 mouse embryonic stem cell line ES129.
9. Incubate cassettes at 37 degrees C. in incubator
10. Monitor cell adhesion by microscopy.

EXAMPLE 3

Polystyrene and Other Carrier Materials

An elastomeric PDMS mold (75 mm×50 mm×0.5 mm) was fabricated by casting PDMS on an SU-8 master fabricated by standard photolithography on a glass slide. The SU-8 thickness was 10-250 μm. Approximately 4 g of polystyrene solution (25 wt % in GBL) was added to the PDMS mold (not shown). This amount of solution generates a film of approximately 0.25 mm thickness after baking Polystyrene solution was found to be dewetting on PDMS surface during baking, causing the solution to shrink. To prevent the dewetting, the PDMS mold was treated with air plasma for 1 min prior to the addition of the polystyrene solution. This treatment did not affect the mold release in the final step. A short (1 min) degas by oil pump was required to remove the trapped air bubbles in the PDMS mold. Since GBL has a high boiling point of 204° C., polystyrene solution did not evaporate or boil during degassing. The polystyrene solution remained as a clear, viscous solution after degassing. The mold was then heated on a hotplate at 150° C. overnight (16 h) to completely evaporate the GBL solvent. Finally, the PDMS/polystyrene was cooled to room temperature and the PDMS mold was slowly peeled from the solidified polystyrene.

Solvents for other materials from which rafts or carriers are fabricated are described in the table below. Composite carriers are conveniently prepared by carrying out the process with a first material, and then sequentially repeating the process one or more times with a different material, until a composite of two or more materials is formed.

TABLE 3

Materials for raft fabrication and liquid micromolding

| Solute | Solvent | Process conditions |
|---|---|---|
| Polystyrene | gamma-Butyrolactone Dimethylformamide N-Methylpyrrolidone | Solidification via solvent evaporation |
| Poly(styrene-co-acrylic acid) | gamma-Butyrolactone Dimethylformamide N-Methylpyrrolidone | Solidification via solvent evaporation |

TABLE 3-continued

Materials for raft fabrication and liquid micromolding

| Solute | Solvent | Process conditions |
|---|---|---|
| Epoxy (e.g. EPON 1002F and 1009F resin) | gamma-Butyrolactone | Solidification via solvent evaporation |
| Biodegradable polymers (e.g. poly(dl-lactide), [1]poly(dl-lactide/glycolide)) | gamma-Butyrolactone | Solidification via solvent evaporation |
| Hydrogel (e.g. polyethylene glycol diacrylate) | Water | Solidification via thermal or photo induced crosslink reaction' |
| Biopolymers (e.g. chitosan, collagen, Matrigel) | Water | Solidification via pH change (e.g. neutralization) |
| Ceramics (e.g. sodium silicate) | Water | Solidification via solvent evaporation |
| Porous materials (e.g. polystyrene, epoxy, poly(dl-lactide)) | gamma-Butyrolactone Dimethylformamide N-Methylpyrrolidone | Solidification through leaching out solvent in a second solvent (e.g. water). Since the solvent is miscible with water, the leaching out of solvent leaves porous structures. Water does not dissolve the material. |
| cyclic olefin copolymer | Propylene glycol methyl ether acetate Anisole Cyclopentanone | Solidification via solvent evaporation |
| polycarbonate | Propylene glycol methyl ether acetate Anisole Cyclopentanone | Solidification via solvent evaporation |
| Poly(methyl methacrylate) | Propylene glycol methyl ether acetate Anisole Cyclopentanone | Solidification via solvent evaporation |

[1]Where it is desired to incorporate live feeder cells into the hydrogel, the feeder cells can be added after crosslinking, or added before crosslinking and photocrosslinking employed.

EXAMPLE 4

Magnetic Carriers and Multi-Layer Carriers

While deforming the PDMS frame during microraft release does not affect adjacent microrafts, we observed that loosely adherent cells can detach and contaminate the collected cell colonies. To overcome this limitation, this example utilizes magnetism to manipulate the microraft. Microrafts are doped with magnetic nanoparticles so they can carry the cell of interest to the collection dish via magnetic attraction. Due to the ability to fabricate microrafts with a variety of polymers outside those required for carrier development an anionic transparent magnetic polystyrene was developed which has better biocompatibility and a lower autofluorescence than magnetic 1002F or SU8 photoresists.

Magnetic microrafts were developed with these polymers and coated with a non-magnetic polymer to provide a barrier between the magnetic film and plated cells. Additional layers of polymer added over pre-existing microrafts remained isolated within the PDMS microwells even after the addition of a forth polymer. Magnetic microrafts were released from the PDMS frame and magnetically collected with an external magnet. Cells grown on magnetic rafts were imaged with traditional transmitted light and fluorescence microscope, as well as confocal microscope. The growth and localization of cells on these microrafts with untreated poly(styrene-co-acrylic acid) (PS-AA) surfaces was monitored. Finally, single cells attached to magnetic microrafts were sorted and magnetically collected.

Materials.

The following materials were obtained from the Aldrich Chemical Company (St. Louis, Mo.): iron(II) chloride tetrahydrate (99%), iron(III) chloride anhydrous (98%), iron (III) nitrate nonahydrate (99+%), 28% ammonium hydroxide solution, oleic acid (90%), toluene (reagent grade), triarylsulfoniumhexafluorophosphate salts, mixed, 50% in propylene carbonate, y-butyralactone (GBL, 99+%), 1-methoxy-2-propanol (1002F developer, 98.5%), glutaraldehyde, Rhodamine B, 2,2'-azobisisobutyionitrile (AIBN, 98%), styrene (≥99%) and acrylic acid (99.5%). EPON resin SU-8 and EPON resin 1002F (phenol, 4,4'-(1-methylethylidene)bis-, polymer with 2,2'-[(1-methylethylidene) bis(4,1-phenyleneoxymethylene]bis-[oxirane]) were obtained from Miller-Stephenson (Sylmar, Calif.). Phenyl red free Dulbecco's Modified Eagle's Medium (DMEM), fetal bovine serum (FBS), IX phosphate buffered saline (PBS), pH 7.4, 0.05% trypsin with EDTA solution and penicillin/streptomycin were received from Invitrogen (Carlsbad, Calif.). Sylgard 184 silicone elastomer kit (PDMS) was received from Dow Corning (Midland, Mich.). Fibronectin extracted and purified from human plasma was obtained from Chemicon International Inc. (Temecula, Calif.). Collagen I from rat tail tendon and Falcon™ Petri dishes were purchased from BD Biosciences (San Jose, Calif.). Polycarbonate plates (12"×12"×0.25") were purchased from McMaster-Carr (Los Angeles, Calif.). Wild-type HeLa cells were purchased from the American Type Culture Collection (ATCC, Manassas, Va.). All other chemicals were procured from Fisher Scientific (Pittsburgh, Pa.).

Magnetic Polystyrene Development.

Magnetite nanoparticles were synthesized by the co-precipitation of iron salts in deionized water by the addition of ammonium hydroxide. The nanoparticles were magnetically decanted and the fluid was replaced with fresh deionized water and iron nitrate. 1 h mixing at 80° C. in the presence of iron nitrate allows for oxidation of nanoparticles to maghemite (A. Bee et al., J. Magn. Magn. Mater. 149, 6-9 (1995)). Magnetically decanting the nanoparticles and replacing the liquid with deionized water gives a magnetic ferrofluid. Maghemite nanoparticles were then made hydrophobic through extraction with oleic acid. The magnetic phase was magnetically decanted and excess oleic acid removed by three washes of ethanol. Oleic acid coated maghemite nanoparticles were then dissolved in toluene (5 g of maghemite/1 L toluene). Poly(styrene-co-acrylic acid) (PS-AA) was prepared by copolymerization of styrene and acrylic acid in gamma-butyrolactone (GBL), as described previously (see, e.g., Y. Wang et al., Lab Chip 10, 2917-24 (2010). Briefly 95 g styrene, 5 g acrylic acid, 0.1 g AIBN and 100 g GBL were mixed in a flask and heated in a 60° C. water bath for 72 h to complete copolymerization. A 1:5 v/v mixture of PS-AA in toluene was slowly added to the maghemite ferrofluid. The toluene was then evaporated (Büchi R200 rotovapor, Flawil, Switzerland) until a thick gel remained. GBL was added to this magnetic polystyrene gel until the desired viscosity for efficient dip coating was achieved.

Fabrication of PDMS Mold.

PDMS molds for the arrays of microrafts were developed though soft lithography from an SU-8 master. The SU-8 masters were developed though typical photolithography experiments as described previously (G. T. Salazar et al, Anal. Chem. 79, 682-7 (2007)). SU-8 masters for raft release and cell culture experiments were composed of 40 μm thick 100×100 μm squares with 20 μm gaps. The SU-8 master for the 4 layer rafts were composed of 100 μm thick 100×100 μm squares with 30 μm gaps which were developed by frontside exposure. Following development, the SU-8 masters were made non-sticky to PDMS by spin coating 1% vol. octyltrichlorosilane in propylene monomethyl ether acetate at 2000 rpm for 30 s, followed by baking at 120° C. on a hotplate for 10 min. PDMS prepolymer (10:1 mixture of base:curing-agent of Sylagard 184 kit) was poured over the SU-8 master and degassed (house vacuum) to remove trapped air bubbles. Following degassing the sample was spin-coated at 500 rpm for 30 s and baked at 100° C. for 30 min which gives a 200 μm-thick PDMS layer over the SU-8 master. The PDMS was then gently peeled from the SU-8 master leaving a PDMS mold containing an array of multiwells.

Fabrication of Magnetic Microrafts.

Releasable magnetic microstructures were micromolded within the microwells of the PDMS mold, as described previously (see, e.g., Y. Wang et al., Lab Chip 10, 2917-24 (2010). For single-layer microraft arrays magnetic 1002F or magnetic poly(styrene-co-acrylic acid) were applied over the PDMS mold. Trapped air bubbles within the microwells were removed though degassing under vacuum (Oerlikon Leyboid pump). The PDMS mold was then strung to a DC motor and lowered into a solution of the magnetic polymer well side down. Slowly raising the PDMS mold gives a convex solution of polymer in each microwell. Placing the PDMS mold in a 95° C. oven for 2 h evaporates the bulk of the GBL giving concave microstructures within the microwells. Further evaporation of the magnetic microstructures is achieved by a 1 h bake at 120° C. vacuum oven (−30 in. Hg). Multi-layer microrafts may be constructed through repeating the above process with different polymers dissolved in GBL.

Following fabrication of the microraft arrays the PDMS mold was placed onto a polycarbonate cassette, microraft array face side down, and the PDMS mold was stretched to reduce any sagging. While still attached to the cassette a second polycarbonate cassette (25.4 mm×25.4 mm×6.35 mm/top release or 25.4 mm×25.4 mm inner×53 mmo.d.×10 mm height/bottom release) was glued to the top of the PDMS mold using PDMS with a 70° C. bake in an oven for 1 h.

Release and Collection of Magnetic Microrafts.

Microrafts on an inverted array were released from the top by means of previously used procedures (see, e.g., Y. Wang et al., Lab Chip 10, 2917-24 (2010). Additionally, magnetic rafts were released with a needle from below the array and magnetically collected against gravity onto a collection plate. The microraft array attached to the release chamber with culture media enclosed within the chamber by a collection plate was directly placed upright on a microscope stage. The release needle, an anodized steel microneedle with a 150 nm base diameter and 17.5 nm tip diameter (Fine Science Tools, Foster City, Calif.) was either bound to a PDMS block or bent at a 90° angle and attached to an XYZ micromanipulator with a polycarbonate brace. The needle tip was positioned between the center of the microscope objective and the microraft of interest. Individual microrafts were released from the PDMS mold by raising the needle to puncture the PDMS and eject the selected microraft. Following release the micromanipulator was lowered to its original position. Released microrafts were drawn to the collection plate by a permanent magnet held above the cassette. The magnet was kept over the collection substrate to retain microrafts as the collection plate is gently lifted off the microraft cassette.

Cell Culture on Magnetic Microrafts.

For quick (2 h) adhesion of cells onto microrafts the array was first treated in a plasma cleaner (Harrick Plasma, Ithaca, N.Y.) for 1 min. The microraft array and cassette holder were thoroughly sprayed with 75% ethanol and allowed to dry in a tissue culture hood. Following sterilization and 3 rinses with sterile DI $H_2O$, 1 mL type I collagen from rat tail (100 μg mL$^{-1}$) was added to the microraft array for 1 h including a 20 min degassing by vacuum to remove trapped air bubbles within the microwells. 3 rinses of DI $H_2O$ was followed by the addition of DMEM supplemented with FBS (10%), L-glutamine (584 mg L$^{-1}$), penicillin (100 units mL$^{-1}$), and streptomycin (100 μg mL$^{-1}$). A suspension of 15,000 cells was then added to the microraft array and allowed to adhere to the microrafts for 2 h in a 37° C. incubator with a 5% $CO_2$ atmosphere.

Prior to cell selection, loose cells were removed with 3 rinses of $H_2O$ and DMEM was added to the microraft chamber. A plasma cleaned and sterilized polystyrene petri dish was then mated to the microraft cassette which made a concealed chamber filled with cell culture media. Following single cell collection the petri dish was removed from the microraft cassette and filled with 3 mL conditioned media and allowed to culture in a 37° C. incubator with a 5% $CO_2$ atmosphere. Conditioned media was made by culturing subconfluent cultures of GFP-HeLa cells in DMEM supplemented with FBS (10%), L-glutamine (584 mg L penicillin (100 units mL$^{-1}$), and streptomycin (100 μg mL$^{-1}$) for 48 h. Cells were centrifuged (3,000×g, 20 min) and the supernatant removed and stored at −20° C. until ready for use.

Results

Single-Layer Magnetic Rafts.

In the current work, microrafts were developed by dip-coating various polymers (SU-8, 1002F and PS-AA) containing 0.01 to 1 wt % uniformly distributed maghemite nanoparticles dissolved in 70 wt % GBL on a PDMS mold consisting of arrays of 100×100 μm squares isolated by 40 μm tall 20 μm wide PDMS walls. To assist in release of the microrafts the SU-8 master was developed by using backside exposure. This creates a slightly bowed sidewall which decreases the sharp contact angle of the microrafts. These polymers showed successful dewetting on the PDMS and microraft construction. Magnetic rafts remain isolated within the PDMS wells and possess a slightly concave surface as monitored by SEM and TEM (not shown). TEM images of vertical slices through microrafts composed of 1% $yFe_2O_3$ in 1002F or PS-AA show that these structures have concave curvatures of 18° and 20°, respectively. The microraft thickness and curvature can be altered by adjusting the concentration of polymer in GBL that is dip-coated.

Transparency of the magnetic polymers is retained during microraft fabrication (not shown). It has previously been shown that magnetic nanoparticles will accumulate at the surface of the polymer during photolithographic processing of magnetic photoresists. Horizontal slices through the magnetic microrafts were imaged by TEM to identify the dispersion of magnetic nanoparticles throughout the microrafts. All microrafts composed of 1% $yFe_2O_3$ in 1002F showed evenly distributed nanoparticles throughout the polymer with a 20 nm thick layer of maghemite nanoparticles accumulated at the surface and bottoms of the microrafts (not shown). These results confirm the previous hypothesis that nanoparticles are carried to the extremities of the polymer by evaporating GBL molecules (P. C. Gach, C. E. Sims and N. L. Allbritton, Biomaterials 31, 8810-17 (2010)). Microrafts developed with 1% $yFe_2O_3$ in PS-AA have uniformly distributed nanoparticles through the polymer, however, unlike the magnetic 1002F there is no accumulation of nanoparticles at the microraft surfaces (not shown). The retention of the nanoparticles within the microrafts is likely due to coordinative bonding between the magnetic nanoparticles and the PS-AA, a phenomenon hypothesized to occur in similar nanocomposites by previous researchers (S. Wei, Y. Zhang and J. Xu. J. Polym. Res. 18, 125-130 (2011)).

Multi-Layer Magnetic Rafts.

In this work we tested the ability to fabricate microrafts containing multiple layers of different polymers. Successful layering is dependent on the should be capability of polymer of dewetting on the microraft surface between the PDMS wells. The surface tension of 1002F and PS-AA are 20 and 25 dyne $cm^{-1}$, respectively, which is still significantly lower than that of the polymer solvent (GBL, 40 dyne $cm^{-1}$). Second, the quantity of polymer coating the microrafts should be high enough to ensure that when the GBL is evaporated the polymer will uniformly coat the microraft.

Figure 13:
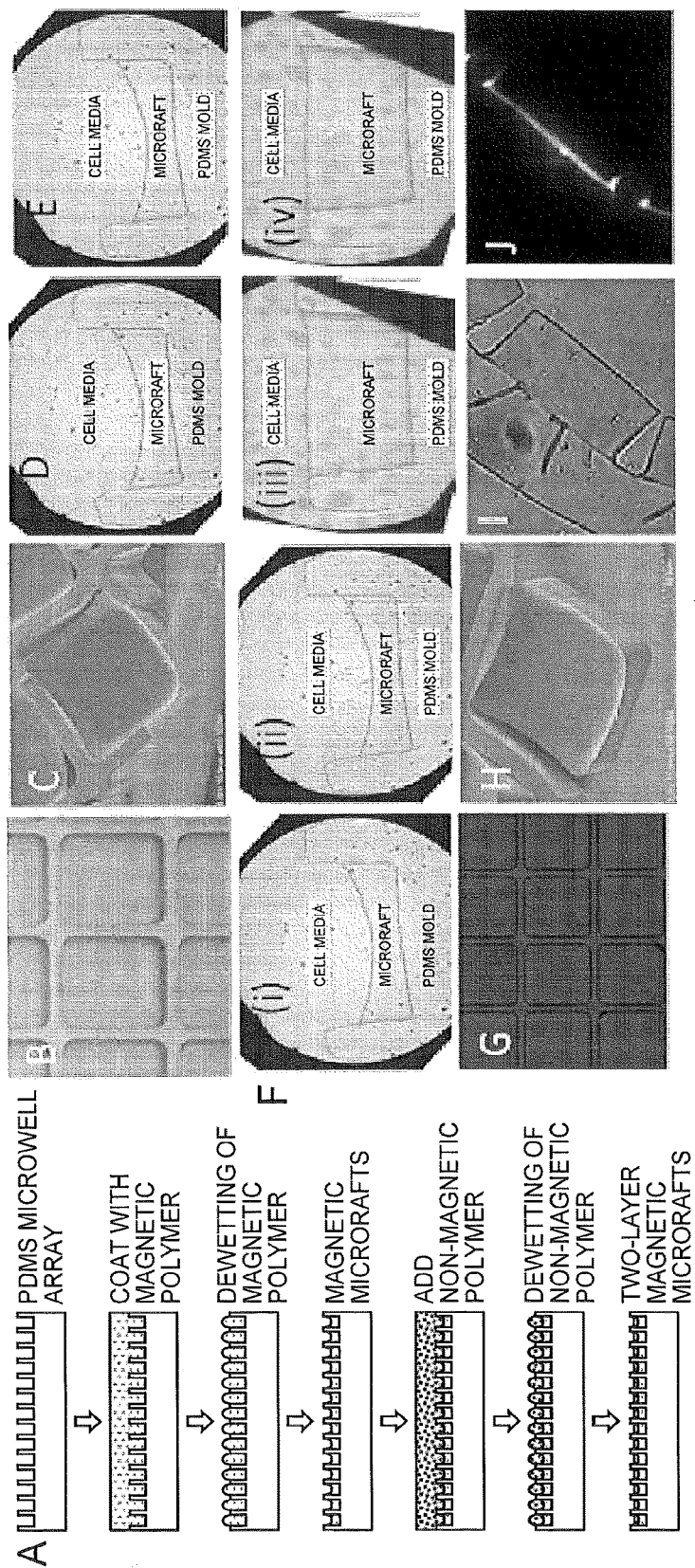
FIG. 13. Scheme of multilayer microraft fabrication. Transmitted light (A) and SEM (B) image of 2 layer microraft composed of a 1% $Fe_2O_3$ embedded in 1002F photoresist bottom and a polystyrene top. TEM image of slice through layers of a 2 layer microraft composed of a 1% $Fe_2O_3$ embedded in 1002F photoresist bottom and a polystyrene top where the polystyrene top is 5 um thick (C) or 20 urn thick (D). TEM image of single-layer magnetic raft (E), 2-layer raft (F), 3-layer raft (G) and 4-layer raft (H). Transmitted light (I) and SEM (J) image of 4-layer microraft.

To fabricate two layer magnetic rafts a magnetic raft array was constructed as described above using 1002F or PS-AA containing 1% $yFe_2O_3$. A layer of PS-AA dissolved in 70 wt % GBL was then coated on the magnetic raft by repeating the fabrication procedure for making the first microraft layer. Following evaporation of solvent a uniform layer of PS-AA is coated on the magnetic raft. The polymer remains isolated within the PDMS wells and the microrafts retain smooth side walls as confirmed by transmitted light microscopy and SEM (FIG. 13A-B). Addition of a second layer did not cause any noticeable light scatter when imaged by transmitted light and fluorescence microscopy. TEM images of vertical sections through the two layer microrafts show the central thickness of the poly(styrene-co-acrylic acid) layer to be 10 µm with a concave curvature of 10° (FIG. 13C). While the viscosities of the polymers used for the first and second layers are the same the second layer is much thinner due to less total polymer filling the PDMS microwells which have been previously filled with a magnetic polymer. Thicknesses of the microraft layers can be adjusted by controlling the volume of polymer within the GBL during dip coating. Addition of poly(styrene-co-acrylic acid) dissolved in 80 wt % GBL gives a second layer thickness of 5 µm with a concave curvature of 15° (FIG. 13D).

Successes in two layer microraft fabrication demonstrate the capabilities of developing microrafts exhibiting multiple properties. To expand upon the fabrication capabilities; microrafts developed with four successive dip coating steps of different polymers were prepared. 1002F, 1002F containing 0.01% Bodipy FL, 1002F containing 1% maghemite nanoparticles and 1002F containing 0.01% Rhodamine B, each dissolved in 70 wt % GBL, were each sequentially dip-coated onto a PDMS mold consisting of arrays of 100×100 µm squares isolated by 40 µm tall 20 µm wide PDMS walls (FIG. 13E-G). The polymer remained isolated within the PDMS walls and optical transparency was retained for these microrafts (FIG. 13I-J). A cross-section of the microrafts imaged by light microscopy shows that the surface has a much less concave surface geometry than single or two layer microrafts with a concave curvature of only 1°. Microrafts were also imaged by confocal fluorescence microscopy to analyze the segregations of each successive layer. A GFP filter set shows Bodipy FL fluorescence isolated at the second layer of the microraft and the mCherry filter set shows a very thin Rhodamine B fluorescent layer at the top of the microraft.

Cell Culture on Magnetic Rafts.

For magnetic microrafts to be proper platforms for sorting individual cells and cell colonies they should be capable of providing both good cellular adhesion and long term growth on the substrate. PS-AA, 1002F and magnetic 1002F have all been shown previously to be biologically compatible substrates (see, e.g., P. C. Gach et al., Biomaterials 31, 8810-17 (2010); Y. Wang et al., Lab Chip 10, 2917-24 (2010); [23]J. H. Pai et al., Anal. Chem. 79, 8774-80 (2007)). These substrates along with the recently developed magnetic PS-AA have all been shown to be good substrates for modifying with extracellular matrices, such as fibronectin and collagen, which allow for quick attachment of cells (<2 hrs). Cells plated on microrafts coated with collagen adhere to the surface after an hour and begin to reach across the surface within 2 hours of plating as observed with transmitted light and SEM (not shown). Cells allowed to culture on these microrafts for 7 days will fill up the microraft and cross over the PDMS wall to adjacent microrafts. PS-AA and magnetic PS-AA have negative surface charges and allow for cellular adhesion without surface modification within 8 hrs of cell plating. Additionally, microrafts developed from these materials do not require plasma treatment or the addition of an extracellular matrix which also modifies the surface of the PDMS walls allowing for cell crossing to adjacent microrafts. Cell colonies grown on these surfaces remain isolated on the microraft surface and within the confines of the PDMS walls.

A layer of native polymer applied over magnetic micropallets was previously shown to provide a protecting layer to prevent nanoparticle uptake by cells (P. C. Gach et al., Biomaterials 31, 8810-17 (2010)). Applying a thin layer of non-magnetic polymer over the magnetic microrafts would remove possible nanoparticle contamination within cells which could disrupt cellular functions important in sensitive biological assays. Furthermore, microrafts fabricated with numerous polymer layers have a much flatter geometry and surfaces flush with the PDMS side walls. These factors could make cells cultured on these microrafts more susceptible to crossing the PDMS gap to adjacent microrafts. Microrafts were developed with 4 successive dip-coating steps with 1002F to create a tall and flat microraft. Following plasma treatment and fibronectin coating, cells loaded on these microrafts showed good initial attachment, however, cells migrated between microrafts within 3 days of culture. Microrafts were also developed by 4 successive dip-coated steps using PS-AA. These microrafts also had flat tops which rose to the level of the PDMS wells. Cell colonies grown on these microrafts remained confined within the PDMS walls 8 days following plating.

Many biological assays rely on fluorescent markers to identify the cell lines of interest. The ability to perform sensitive fluorescence measurements on multi-layer magnetic rafts was demonstrated by examining cells loaded with fluorescence dyes with fluorescence and confocal microscopy. Cells stained with a nuclear dye (Hoechst 33342, excitation/emission 350/461 nm) and a dye loaded in the cytoplasm (CellTracker Green, excitation/emission 492/517 nm) were plated on the two-layer magnetic microrafts. The Hoechst 33342 was clearly isolated within the nucleus of the cells and CellTracker Green exhibited good fluorescence with no background scatter or distortion caused by imaging through the microraft (not shown).

Release and Collection of Magnetic Microrafts.

Figure 14:
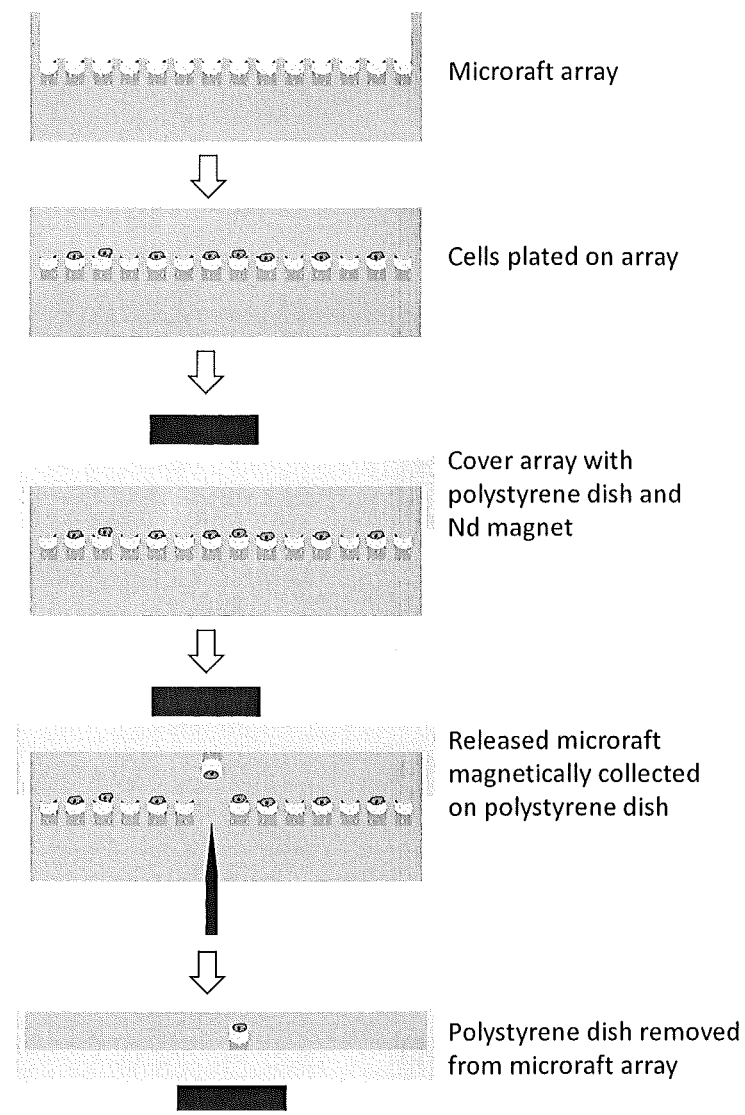
FIG. 14. Scheme for the magnetic collection of microrafts.

Utility of magnetic microrafts relies upon the ability to selectively release and manipulate the microrafts with an external magnet. One example for collecting microrafts is schematically illustrated in FIG. 14. Magnetic microrafts were prepared for release by attaching the microraft array to a polycarbonate chamber, as described previously (see, e.g., Y. Wang et al., Lab Chip 10, 2917-24 (2010)). The chamber was filled with DMEM supplemented with 10% FBS and matted to a second polycarbonate cassette attached to a glass slide. Three methods were developed for releasing and magnetically collecting individual 100×100 μm square microrafts (40 1 μm tall 20 μm wide PDMS walls) from the microraft array with a microneedle (17.5 μm tip diameter). The efficiency of collection of these loose magnetic microstructures was then quantified by varying the magnetic field strength and the concentration of maghemite within the microrafts: data are given in Table 4 below.

al., Lab. Chip 10, 2917-24 (2010)). As schematically illustrated in FIG. 14, a permanent magnet was held under the collected microrafts as the microraft array was replaced with a glass slide attached to a polycarbonate cassette. The permanent magnet was then removed and placed over the collection glass. Gentle agitation of the glass holding the microrafts frees the magnetic microrafts and allows for magnetic collection against gravity onto the collection substrate if the magnetic force experienced by the microrafts is sufficient. Microrafts containing 1% maghemite were collected with 100% efficiency with magnet displacements up to 18 mm from the initial position, corresponding to a magnetic field of 27 mT. Increasing the height of the collection substrate to 22 mm (18 mT) lowers the collection probability to 15±0. Decreasing the concentration of maghemite in the microrafts to 0.1% results in collection efficiencies of 100±0, 53±26 and 17±8 with magnet separations of 6, 8 and 10 mm (166, 113 and 79 mT), respectively. Furthermore, microrafts containing 0.01% maghemite were collected with 76±27 and 10±5% efficiencies at magnet separations of 1 and 2 mm (449 and 352 mT), respectively. Likewise, 2-layer microrafts composed of 1% magnetic 1002F bottoms and PS-AA tops resulted in collection probabilities of 100% at distances up to 14 mm (44 mT) and 62±26% at 18 mm (27 mT). This method shows the ability to obtain pure microrafts where an initial magnetic collection is not feasible.

Along with purifying collected microrafts, magnetism can be utilized to vertically collect magnetic microrafts immediately following release. Placing the microraft cassette in an upright orientation on an open microscope stage allows for access of the microneedle for release from the bottom-up. Two approaches were successfully applied to release the microrafts in this orientation. In the first method, the microneedle was attached to the XYZ micromanipulator with a U brace to position the needle beneath the microraft array. Bending the microneedle at a 90° angle prior to

TABLE 4

Magnetic collection of rafts.

| Raft Material | Pallet/Magnet Separation (mm) | B Field at Pallet Array | Collection Probability (%) Bottom Release | Collection Probability (%) Top Release Purification |
|---|---|---|---|---|
| Native 1002F | 1 | 449 ± 4 | 0 ± 0 | 0 ± 0 |
| 0.01% Fe2O3 in 1002F | 1 | 449 ± 4 | 46 ± 15 | 76 ± 27 |
|  | 2 | 352 ± 10 | 0 ± 0 | 10 ± 5 |
| 0.1% Fe2O3 in 1002F | 6 | 166 1 6 | 100 ± 0 | 100 ± 0 |
|  | 8 | 113 ± 7 | 24 ± 8 | 53 ± 26 |
|  | 10 | 79 ± 3 | 0 ± 0 | 17 ± 8 |
| 1% Fe2O3 in 1002F | 6 | 166 ± 6 | 100 ± 0 | 100 ± 0 |
|  | 10 | 79 ± 3 | 100 ± 0 | 100 ± 0 |
|  | 14 | 44 ± 3 | 100 ± 0 | 100 ± 0 |
|  | 18 | 27 ± 2 | 100 ± 0 | 100 ± 0 |
|  | 22 | 18 ± 2 | N/A | 15 ± 4 |
| 1% Fe2O3 in 1002F bottom Native PS-AA Top | 6 | 166 ± 6 | 100 ± 0 | 100 ± 0 |
|  | 10 | 79 ± 3 | 100 ± 0 | 100 ± 0 |
|  | 14 | 44 ± 3 | 100 ± 0 | 100 ± 0 |
|  | 18 | 27 ± 2 | 82 ± 15 | 95 ± 5 |
|  | 22 | 18 ± 2 | N/A | 0 ± 0 |

Magnetism can provide a method for purifying magnetic microrafts from cell debris and other contamination that may fall down during the gravity based collection utilized during top-down release of microrafts. Microrafts were released and allowed to fall down to the initial collection plate with the same protocol as used previously (see, e.g., Y. Wang et attachment to the brace displaces the equipment from the objectives optical path and reduces light scatter by the equipment. This method allows for the integration of a motorized release system. As a low-cost alternative, the microraft needle was mounted onto a PDMS block which could be placed over the microscope objective of an inverted microscope. Raising the microscope objective provides the z-axis manipulation of the microneedle required to dislodge the microraft.

Placing the external magnet over the collection substrate allows for immediate collection following release of the selected microrafts (not shown). Microrafts containing 1% maghemite were collected with 100% efficiency at distances up to 18 mm (27 mT) the maximum achievable collection plate separation with the current system. Microrafts with maghemite concentrations of 0.1% were collected with 100±0, 24±8 and 0±0% efficiencies at magnet separations of 6, 8 and 10 mm (166, 113 and 79 mT), respectively. Microrafts with only 0.01% maghemite exhibited a collection probability of 46±15% at a magnet separation of 1 mm (449 mT). the addition of a PS-AA layer over the 1% maghemite loaded microraft lowered the collection efficiency with a magnet displacement of 18 mm (27 mT) to 82±15%. Slightly higher collection efficiencies were observed for the agitated microrafts with respect to the immediately collected microrafts. This could be a result of these agitated microrafts rising further up the collection plate prior to being caught in a high magnetic field. Releasing microrafts from the bottom has the advantage in that it allows for a one-step collection without requiring plate transfers which is a simpler method and lowers the stresses cells encounter during fluid exchanges.

Cell Sorting and Purification with Magnetic Microrafts.

Utility of magnetic microrafts for bioanalytical applications was demonstrated by sorting single highly fluorescent HeLa cells from a heterogeneous population of GFP-HeLa cells exhibiting various degrees of fluorescence spiked with HeLa cells at a 3:1 ratio. In triplicate experiments, 15,000 cells were plated on an array of 44,000 two-layer microrafts (PS-AA top/1% magnetic PS-AA bottom −100×100 μm square 40 μm tall PDMS wells 20 μm gap) attached to a 10 mm tall polycarbonate cassette designed to fit a 53 cm round polystyrene petri dish bottom. Three hours following cell plating, 30 microrafts containing single cells exhibiting high fluorescence were released from the bottom and magnetically collected into individual petri dishes (not shown). Following microraft collection the chamber was transferred to a sterile environment where the petri dish could be removed from the microraft cassette and filled with fresh media and covered with the petri dish top. Keeping the magnet held under the petri dish during this process helps retain the microraft at the center of the petri dish during the separation and wash steps. Immediately following collection the petri dish was imaged for the presence of the collected microraft. All 30 microrafts were collected and retained their single cell following collection (not shown). Following a 7 day incubation period 97±3% of single cells grew into a colony (not shown).

The ability to purify previously sorted microrafts was demonstrated by releasing 20 magnetic microrafts from the top and magnetically purifying the microrafts, as described previously. Again, 3,750 GFP-HeLa cells and 11,250 HeLa cells were plated on an array of 44,000 two-layer microrafts (PS-AA top/1% magnetic PS-AA bottom 100×100 μtm square 40 μm tall PDMS wells 20 μm gap) attached to a 6 mm tall polycarbonate cassette. All 20 microrafts were gravitationally collected and then magnetically collected on a glass collection substrate. Each microraft retained its single cell immediately following collection and 18 of cells grew into a colony after 7 days of incubation. All substrates from magnetic collection and magnetic purification showed no sign of contamination of unwanted cells when imaged after 7 days of incubation. The initial glass slide used for gravity collection showed 11 distinct cell colonies after being observed following 7 days of incubation. These results show that the magnetic collection of microrafts is an excellent method for obtaining pure populations of cells from a heterogeneous population.

Mounting the Release Needle on the Microscope Objective.

Figure 15:
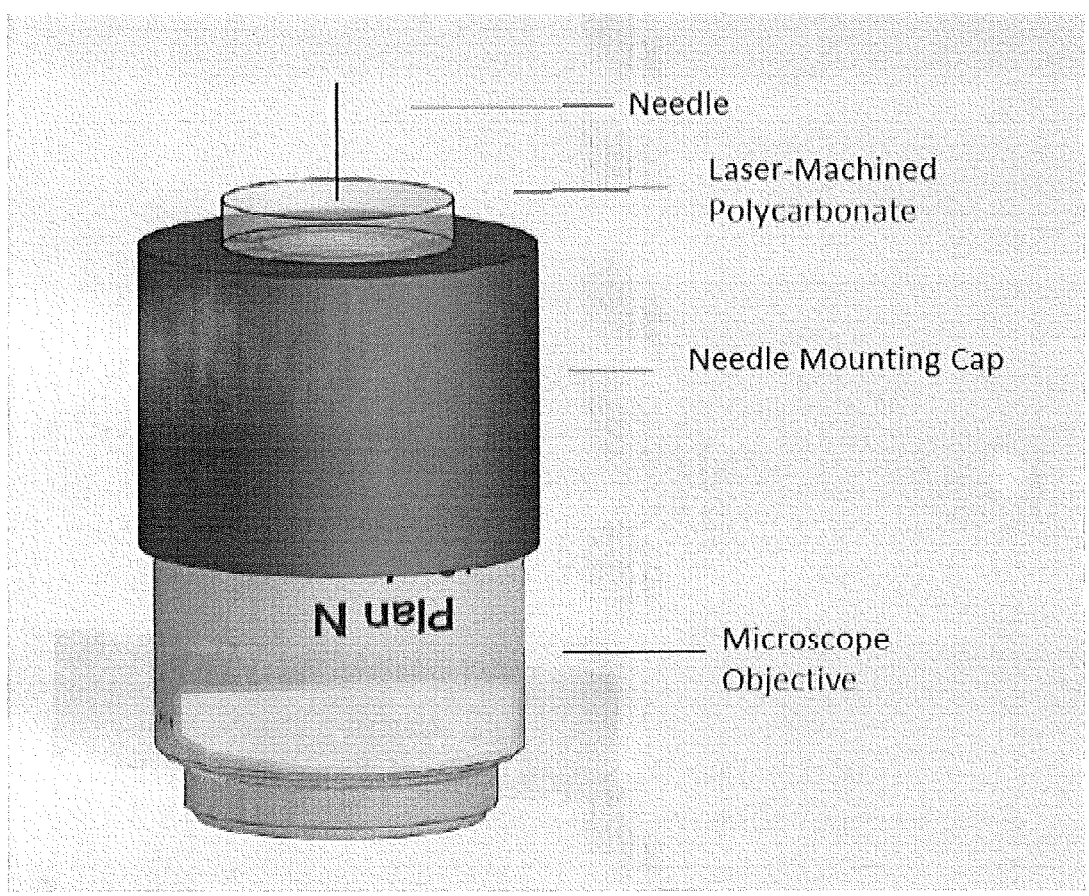
FIG. 15. A perspective view of a first embodiment of a microscope objective and probe assembly of the present invention.

In another embodiment for using a microscope objective to provide the z-axis manipulation of the needle to dislodge a microraft, a suitable needle is inserted into a cavity in a small transparent polycarbonate plate or other suitable material. Then the polycarbonate plate with fixed needle is attached or mounted to the microscope objective. For example, a polycarbonate plate is machined by high precision milling or laser ablation to produce a hole 10-15% larger in diameter than the needle to be mounted. The base of the needle is dipped in an adhesive and inserted into the machined hole. A cylindrical cap made from a suitable material, such as a thermoplastic or polystyrene, is designed and manufactured by 3D printing or injection molding or other means to a dimension that provides a friction fit to a microscope objective, which can be readily achieved once the diameter and length of the objective is known. The polycarbonate plate is secured to the top of the cylindrical cap and the assembly is mounted onto the microscope objective (FIG. 15). The resulting release assembly is inexpensive and minimally disruptive to the functioning of the microscope and the imaging of the microrafts while taking advantage of the focusing mechanism of the microscope to provide the movement of the release needle.

Figure 16:
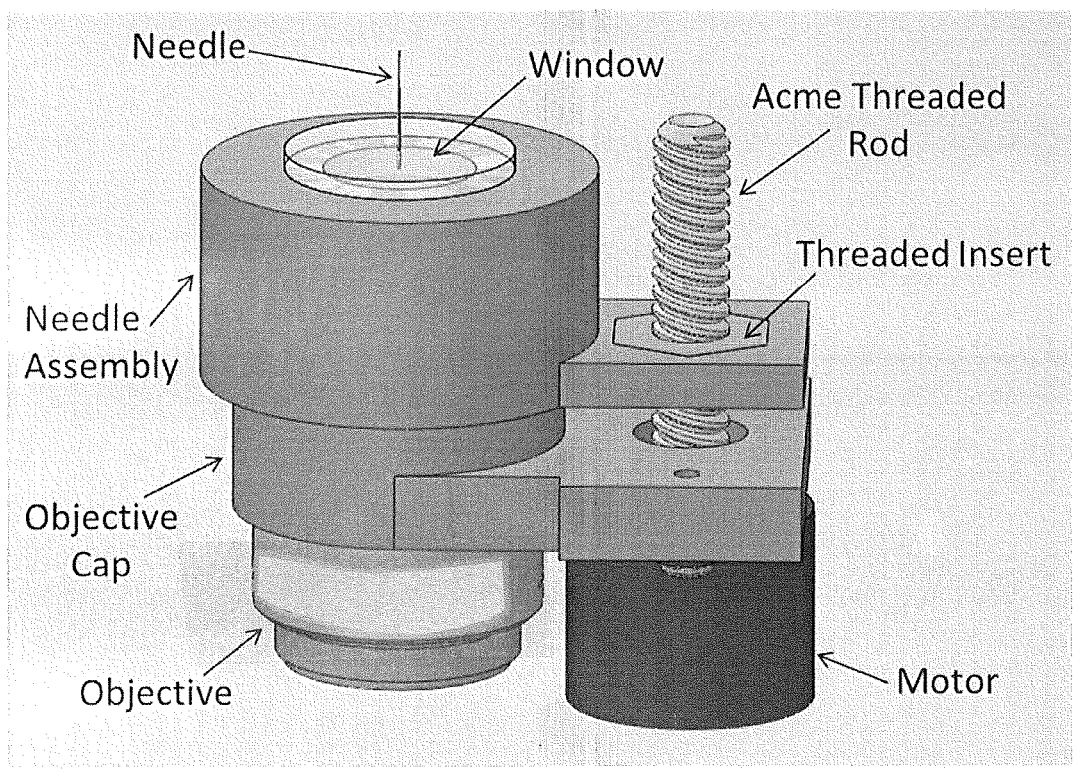
FIG. 16. A perspective view of a second embodiment of a microscope objective and probe assembly of the present invention.

A release needle mounted or attached to a microscope objective may also incorporate a motorized device to achieve a greater needle displacement than can be achieved by movement of the microscope objective, or it can be used to move the release needle without changing the focusing of the objective on the microraft array. In one embodiment, a motorized release system is composed of a first cylindrical cap made from a suitable material that is designed and manufactured to a dimension that provides a friction fit to a microscope objective, and further providing a flange to which is mounted a motor having a screw drive that is oriented upwards from the flange (FIG. 16). A second cap is designed and manufactured to fit over the top of the first cap and to move freely in the z-axis direction relative to the first cap. The second cap is further provided with a polycarbonate (or other suitable material) plate to which a needle is attached, and a flange to which is attached a fitting that engages with the screw drive, such that the turning action of the screw drive caused by the motor will in turn cause the second cap to move in a controlled manner and thus provide z-axis manipulation of the needle. (FIG. 16).

Figure 17:
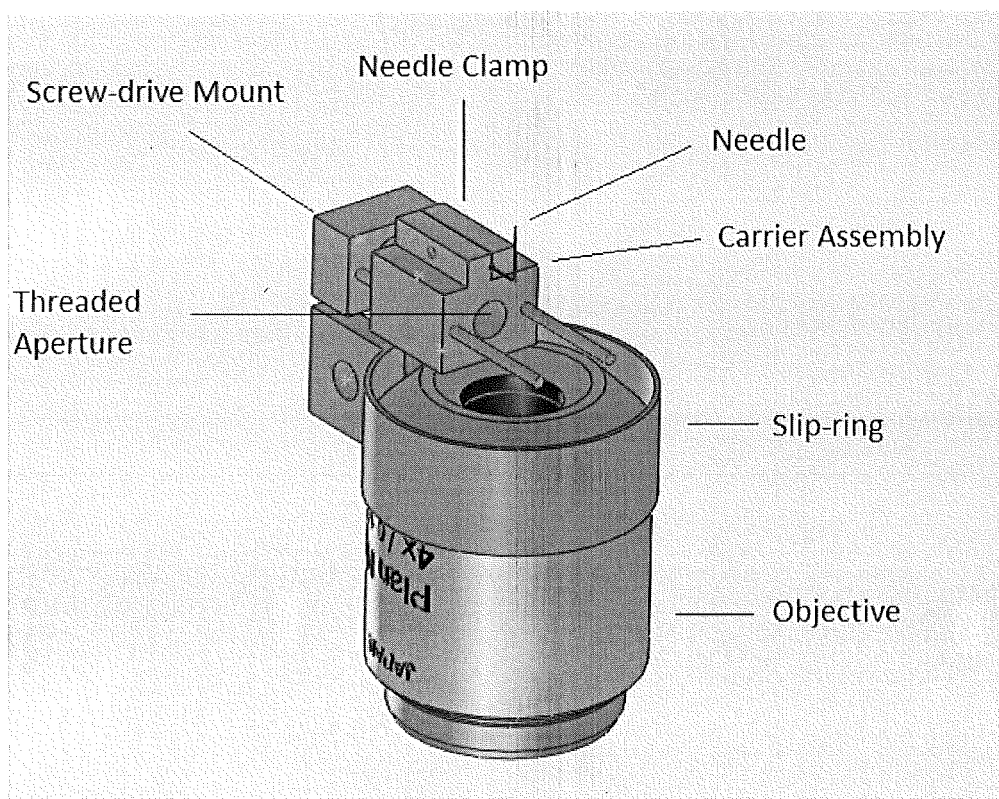
FIG. 17. A perspective view of a third embodiment of a microscope objective and probe assembly of the present invention.

In another embodiment of a motorized device for a release needle assembly, a collar made from a suitable material such as plastic or metal is designed to fit around a microscope objective to which is attached a carrier assembly for a needle. (FIG. 17). The needle has a ninety degree bend and is clamped into the carrier assembly such that the elbow of the needle remains at a suitable distance from the carrier assembly to ensure that the carrier assembly does not obstruct the view of the microraft array through the microscope objective. The carrier assembly is mounted to a collar that can either be tightened around the microscope objective or can be designed and manufactured to a dimension that provides a friction fit to the microscope objective. A motor having a screw drive is attached to the collar, and the screw drive engages the carrier by means of a threaded aperture so that the carrier can be translated through one axis of motion into and out of the field of view allowing alignment of the needle to the center of the field of view. Translation of the needle in the z-axis to release a microraft from an array is accomplished by movement of the microscope objective through the focusing mechanism of the microscope.

When preparing a needle release assembly for use mounted or attached to a microscope objective, a needle may be preferred or selected that is less than the working distance of the objective, but greater than the minimum distance between the objective and the stage. This allows for the needle to alternately puncture the PDMS substrate and release microrafts while being short enough to be removed from the PDMS by the movement of the objective so that the microscope stage can be moved without the stage or PDMS substrate contacting the needle. It is also preferred that the distance between the focal plane of the objective and the tip of the needle be sized or dimensioned (e.g., about 100 times or more of the depth-of-field of the objective) to ensure that the needle itself is not seen in the focused image. As an example, for a typical 10× magnification objective this distance is about 850 micrometers or more.

In one example of mounting a needle to a polycarbonate block, a machined ⅛" thick polycarbonate plate is used to mount the needle vertically on the objective cap. A needle having an outer diameter at the needle base is 150 micrometers is selected, and a hole in the polycarbonate plate is machined to an inner diameter of 165 micrometers. This eases the process of inserting the needle into the plate and restricts the maximum tilt angle of the needle to 0.28 degrees, minimizing off-axis stress on the needle over repeat punches and extending its lifetime. The needle is glued into the machined polycarbonate plate with a clear adhesive closely matching the index of refraction of the polycarbonate (1.4-1.6). This can minimize distortion of the image through the objective that may be caused by the machined hole in the polycarbonate plate through reducing refraction and edge scatter off of the machined surfaces. PDMS or a clear epoxy are examples of suitable materials for such purposes.

REFERENCES

1. Patel, D., *Separating Cells*. Springer-Verlag: New York, 2001; p 168.
2. Fu, A. Y.; Chou, H. P.; Spence, C.; Arnold, F. H.; Quake, S. R., An integrated microfabricated cell sorter. *Anal Chem* 2002, 74, (11), 2451-2457.
3. Wolff, A.; Perch-Nielsen, I. R.; Larsen, U. D.; Friis, P.; Goranovic, G.; Poulsen, C. R.; Kutter, J. P.; Telleman, P., Integrating advanced functionality in a microfabricated high-throughput fluorescent-activated cell sorter. *Lab Chip* 2003, 3, (1), 22-27.
4. Young, S. M.; Curry, M. S.; Ransom, J. T.; Ballesteros, J. A.; Prossnitz, E. R.; Sklar, L. A.; Edwards, B. S., High-throughput microfluidic mixing and multiparametric cell sorting for bioactive compound screening. *J Biomol Screen* 2004, 9, (2), 103-111.
5. Sohn, L. L.; Saleh, O. A.; Facer, G. R.; Beavis, A. J.; Allan, R. S.; Notterman, D. A., Capacitance cytometry: measuring biological cells one by one. *proceedings of the National Academy of Science, USA* 2000, 97, (20), 10687-90.
6. Wang, X. B.; Yang, J.; Huang, Y.; Vykoukal, J.; Becker, F. F.; Gascoyne, P. R., Cell separation by dielectrophoretic field-flow-fractionation. *Analytical Chemistry* 2000, 72, (4), 832-839.
7. Wclm, B.; Bchbod, F.; Goodell, M. A.; Rosen, J. M., Isolation and characterization of functional mammary gland stem cells. *Cell Prolif* 2003, 36 Suppl 1, 17-32.
8. Burridge, K.; Chrzanowska-Wodnicka, M., Focal adhesions, contractility, and signaling. *Annual Review of Cell and Developmental Biology* 1996, 12, 463-519.
9. Chiquet, M.; Matthisson, M.; Koch, M.; Tannheimer, M.; Chiquet-Ehrismann, R., Regulation of extracellular matrix synthesis by mechanical stress. *Biochemistry and Cell Biology* 1996, 74, 737-744.
10. Ingber, D. E., Tensegrity: the architectural basis of cellular mechanotransduction. *Annual Review of Physiology* 1997, 59, 575-599.
11. Seidl, J.; Knuechel, R.; Kunz-Schughart, L. A., Evaluation of membrane physiology following fluorescence activated or magnetic cell separation. *Cytometry* 1999, 36, (2), 102-111.
12. Piercy, K. T.; Donnell, R. L.; Kirkpatrick, S. S.; Mundy, B. L.; Stevens, S. L.; Freeman, M. B.; Goldman, M. H., Effect of harvesting and sorting on beta-1 integrin in canine microvascular cells. *J Surg Res* 2001, 100, (2), 211-216.
13. Mackie, E. J.; Pagel, C. N.; Smith, R.; de Niese, M. R.; Song, S. J.; Pike, R. N., Protease-activated receptors: a means of converting extracellular proteolysis into intracellular signals. *IUBMB Life* 2002, 53, 277-281.
14. Miki, M.; Nakamura, Y.; Takahashi, A.; Nakaya, Y.; Eguchi, H.; Masegi, T.; Yoneda, K.; Yasouka, S.; Sone, S., Effect of human airway trypsin-like protease on intracellular free $Ca^{2+}$ concentration in human bronchial epithelial cells. *Journal of Medical Investigation* 2003, 50, 95-107.
15. Burgess, D. S., Laser microdissection: Making inroads in research. *Biophotonics International* 2004, 11, 46-49.
16. Todd, R.; Lingen, M. W.; Kuo, W. P., Gene expression profiling using laser capture microdissection. *Expert Rev Mol Diagn* 2002, 2, (5), 497-507.
17. Schutze, K.; Posl, H.; Lahr, G., Laser micromanipulation systems as universal tools in cellular and molecular biology and in medicine. *Cell Mol Biol (Noisy-le-grand)* 1998, 44, (5), 735-746.
18. Burgemeister, R., New aspects of laser microdissection in research and routine. *Journal of Histochemistry and Cytochemistry* 2005, 53, 409-412.
19. Wang, Y.; Sims, C. E.; Marc, P.; Bachman, M.; Li, G. P.; Allbritton, N. L., Micropatterning of living cells on a heterogeneously wetted surface. *Langmuir* 2006, 22, 8257-8262.
20. Salazar, G. T.; Wang, Y.; Young, G.; Bachman, M.; Sims, C. E.; Li, G. P.; Allbritton, N. L., Micropallet arrays for the separation of single, adherent cells. *Analytical Chemistry* 2007, 79, 682-687.
21. Wang, Y.; Young, G.; Bachman, M.; Sims, C. E.; Li, G. P.; Allbritton, N. L., Collection and expansion of single cells and colonies released from a micropallet array. *Analytical Chemistry* 2007, 79, 2359-2366.
22. Wang, Y.; Young, G.; Aoto, P.; Pai, J.-H.; Bachman, M.; Li, G. P.; Sims, C. E.; Allbritton, N. L., Broadening cell selection criteria with micropallet arrays of adherent cells. *Cytometrny A* 2007, 71A, (10), 866-874.
23. Wang, Y.; Salazar, G. T.; Pai, J. H.; Shadpour, H.; Sims, C. E.; Allbritton, N. L., Micropallet arrays with poly (ethylene glycol) walls. *Lab on a Chip* 2008, 8, 734-740.
24. Pai, J.-H.; Wang, Y.; Salazar, a T.; Sims, C. E.; Bachman, M.; Li, G. P.; Allbritton, N. L., Photoresist with low fluorescence for bioanalytical applications. *Analytical Chemistry* 2007, 79 8774-8780.

25. Wang, Y.; Bachman, M.; Sims, C. E.; Li, G. P.; Allbritton, N. L., Simple photografting method to chemically modify and micropattern the surface of SU-8 photoresist. *Langmuir* 2006, 22, (6), 2719-2725.
26. Wang, Y.; Pai, J.-H.; Lai, H. H.; Sims, C. E.; Bachman, M.; Li, G. P.; Allbritton, N. L., Surface graft polymerization of SU-8 for bio-MEMS applications. *Journal of Micromechancis and Microengineering* 2007, 17, 1371-1380.
27. Shadpour, H.; Sims, C. E.; Thresher, R. J.; Allbritton, N. L., Sorting and Expansion of Murine Embryonic Stem Cell Colonies Using Micropallet Arrays. *CYTOMETRY PART A* 2009, 75A, (2), 121-129.
28. Shadpour, H.; Sims, C. E.; Allbritton, N. L., Enrichment and Expansion of Cells Using Antibody-Coated Micropallet Arrays *CYTOMETRY PART A* 2009, 75A, (7), 609-618.
29. Salazar, G. T.; Wang, Y.; Sims, C. E.; Bachman, M.; Li, G. P.; Allbritton, N. L., Characterization of the laser-based release of micropallets from arrays. *Journal of Biomedical Optics* 2008, 13, (3), 034007.
30. Microchem Products, Datasheet, T. SU-8 Photoresist Formulations (Rev. February/2002).
31. Chang, S. S., Heat of reaction and curing of epoxy resin. *Journal of Thermal Analysis and calorimetry* 1988, 34, (1), 135-154.
32. Falconnet, D.; Csucs, G.; Grandin, H. M.; Textor, M., Surface engineering approaches to micropattern surfaces for cell-based assays. *Biomaterials* 2006, 27, (16), 3044-3063.
33. Kim, S. M.; Lee, S. H.; Suh, K. Y., Cell research with physically modified microfluidic channels: A review. *Lab on a Chip* 2008, 8, (7), 1015-1023.
34. Rettig, J. R.; Folch, A., Large-scale single-cell trapping and imaging using microwell arrays. *Analytical Chemistry* 2005, 77, (17), 5628-5634.
35. Love, J. C; Ronan, J. L.; Grotenbreg, G. M.; van der Veen, A. G.; Ploegh, H. L., A microengraving method for rapid selection of single cells producing antigen-specific antibodies. *Nature Biotechnology* 2006, 24, 703-707.
36. Mohr, J. C.; de Pablo, J. J.; Palecek, S. P., 3-D microwell culture of human embryonic stem cells *Biomaterials* 2006, 27, (36), 6032-6042
37. Moeller, H. C.; Mian, M. K.; Shrivastava, S.; Chung, B. G.; Khademhosseini, A., A microwell array system for stem cell culture. *Biomaterials* 2008, 29, (6), 752-763.
38. Kovac, J. R.; Voldman, J., Intuitive, Image-Based Cell Sorting Using Opto-fluidic Cell Sorting. *Analytical Chemistry* 2007, 79, 9321-9330.
39. Luo, C. X.; Li, H.; Xiong, C. Y.; Peng, X. L.; Kou, Q. L.; Chen, Y.; Ji, H.; Ouyang, Q., The combination of optical tweezers and microwell array for cells physical manipulation and localization in microfluidic device. *Biomedical Microdevices* 2007, 9, (4), 573-578.
40. Lee, J. N.; Park, C.; Whitesides, G. M., Solvent compatibility of poly(dimethylsiloxanc)-based microfluidic devices. *Analytical Chemistry* 2003, 75, (23), 6544-6554.
41. Dektar, J. L.; Hacker, N. P., Photochemistry of triarylsulfonium salts. *Journal of the American Chemical Society* 1990, 112, (16), 6004-6015.
42. Piruska, A.; Nikcevic, I.; Lee, S. H.; Ahn, C.; Heineman, W. R.; Limbach, P. A.; Seliskar, C. J., The autofluorescence of plastic materials and chips measured under laser irradiation. *Lab on a Chip* 2005, 5, (12), 1348-1354.

The foregoing is illustrative of the present invention, and is not to be construed as limiting thereof. The invention is defined by the following claims, with equivalents of the claims to be included therein.

That which is claimed is:

1. An apparatus for use in releasing a carrier from a microarray with the aid of a microscope, the apparatus comprising:
    a microscope objective including a lens and an optical axis;
    a probe adapted for releasing said carrier when contacting said microarray;
    a retainer formed on or connected to said probe, said retainer configured for engaging said microscope objective in a configuration in which said probe is aligned with said optical axis of said microscope objective; and
    a drive assembly interconnecting said retainer with said microscope objective, wherein said drive assembly moves said retainer relative to said microscope objective while maintaining alignment of said probe with said optical axis.

2. The apparatus of claim 1, wherein said retainer defines an opening adapted to receive said microscope objective.

3. The apparatus of claim 1, wherein the drive assembly comprises a collar member secured to said microscope objective, and a motor interconnecting the collar member and the retainer for driving movement of the retainer relative to the collar member.

4. An apparatus for use in releasing a carrier from a microarray with the aid of a microscope, the apparatus comprising:
    a microscope objective including a lens and an optical axis;
    a probe adapted for releasing said carrier when contacting said microarray;
    a retainer formed on or connected to said probe, said retainer configured for engaging said microscope objective in a configuration in which said probe is aligned with said optical axis of said microscope objective; and
    a transparent mount connected to said retainer, wherein the mount is configured to overlie the lens when the retainer is engaging said microscope objective, and wherein said probe is connected to said mount.

5. The apparatus of claim 4, wherein said retainer defines an opening adapted to receive said microscope objective.

6. An apparatus for use in releasing a carrier from a microarray with the aid of a microscope, the apparatus comprising:
    a microscope objective including a lens and an optical axis, said microscope objective adapted to be movable in a direction toward or away from the microarray;
    a probe adapted for releasing said carrier when contacting said microarray; and
    a retainer formed on or connected to said probe, said retainer configured for engaging said microscope objective in a configuration in which said probe is aligned with said optical axis of said microscope objective, wherein said retainer moves with said microscope objective for contacting said probe with, or disengaging said probe from, said microarray.

7. The apparatus of claim 6, wherein said retainer defines an opening adapted to receive said microscope objective.

8. An apparatus for use in releasing a carrier from a microarray with the aid of a microscope, the apparatus comprising:
    a microscope objective including a lens and an optical axis;

probe adapted for releasing said carrier when contacting said microarray;

a retainer formed on or connected to said probe, said retainer defining an opening for receiving said microscope objective in a configuration in which said probe is aligned with said optical axis of said microscope objective; and a transparent mount connected to said retainer, said mount configured for at least partially closing said opening at one end of said retainer and overlying said lens when said retainer receives said microscope objective, and wherein said probe is connected to said mount.

9. An apparatus for use in releasing a carrier from a microarray with the aid of a microscope, the apparatus comprising:

a microscope objective including a lens and an optical axis;

probe adapted for releasing said carrier when contacting said microarray; and a retainer formed on or connected to said probe, said retainer configured for engaging said microscope objective in a configuration in which said probe is aligned with said optical axis of said microscope objective; and a drive assembly interconnecting said retainer and said microscope objective, wherein said drive assembly moves said retainer transversely relative to said optical axis of said microscope objective for aligning said probe with said optical axis.

10. The apparatus of claim 9, wherein the drive assembly comprises a collar member secured to said microscope objective, and a motor interconnecting the collar member and the retainer for driving movement of the retainer relative to the collar member.

* * * * *